United States Patent
Sun et al.

(10) Patent No.: US 10,361,118 B2
(45) Date of Patent: Jul. 23, 2019

(54) ORGANOMETALLIC PRECURSORS, METHODS OF FORMING A LAYER USING THE SAME AND METHODS OF MANUFACTURING SEMICONDUCTOR DEVICES USING THE SAME

(71) Applicant: Samsung Electronics Co., Ltd., Suwon-si, Gyeonggi-do (KR)

(72) Inventors: Chang-Woo Sun, Hwaseong-si (KR); Ji-Eun Yun, Hwaseong-si (KR); Jae-Soon Lim, Seoul (KR); Youn-Joung Cho, Hwaseong-si (KR); Myong-Woon Kim, Daejeon (KR); Kang-Yong Lee, Daejeon (KR); Sang-Ick Lee, Daejeon (KR); Sung-Woo Cho, Daegu (KR)

(73) Assignees: Samsung Electronics Co., Ltd., Gyeonggi-do (KR); DNF Co. Ltd., Daejon (KR)

( * ) Notice: Subject to any disclaimer, the term of this patent is extended or adjusted under 35 U.S.C. 154(b) by 117 days.

(21) Appl. No.: 15/498,945

(22) Filed: Apr. 27, 2017

(65) Prior Publication Data
US 2018/0102284 A1 Apr. 12, 2018

(30) Foreign Application Priority Data
Oct. 7, 2016 (KR) .................... 10-2016-0129937

(51) Int. Cl.
*H01L 21/768* (2006.01)
*C07F 11/00* (2006.01)
*H01L 21/285* (2006.01)
*C07F 17/00* (2006.01)

(52) U.S. Cl.
CPC ........ *H01L 21/76841* (2013.01); *C07F 11/00* (2013.01); *C07F 17/00* (2013.01); *H01L 21/28562* (2013.01)

(58) Field of Classification Search
CPC ......................... C07F 11/00; H01L 21/76841
See application file for complete search history.

(56) References Cited

U.S. PATENT DOCUMENTS

| 5,077,091 A | 12/1991 | Nowak et al. |
| 6,491,978 B1 * | 12/2002 | Kalyanam ............... C23C 16/18 257/E21.17 |
| 6,552,209 B1 | 4/2003 | Lei et al. |
| 6,911,516 B1 | 6/2005 | Mihan et al. |
| 7,544,826 B2 | 6/2009 | Mihan et al. |
| 7,674,715 B2 | 3/2010 | Kori et al. |

(Continued)

FOREIGN PATENT DOCUMENTS

| JP | 1997199445 A | 7/1997 |
| JP | 2007182443 A | 7/2007 |

(Continued)

OTHER PUBLICATIONS

Royo Organometallics 2007 V26 p. 3831-3839 (Year: 2007).*

*Primary Examiner* — Joseph A Miller, Jr.
(74) *Attorney, Agent, or Firm* — Harness, Dickey & Pierce, P.L.C.

(57) ABSTRACT

An organometallic precursor includes tungsten as a central metal and a cyclopentadienyl ligand bonded to the central metal. A first structure including an alkylsilyl group or a second structure including an allyl ligand is bonded to the cyclopentadienyl ligand or bonded to the central metal.

7 Claims, 18 Drawing Sheets

(56) References Cited

U.S. PATENT DOCUMENTS

| | | |
|---|---|---|
| 7,679,133 B2 | 3/2010 | Son et al. |
| 7,754,908 B2 | 7/2010 | Reuter et al. |
| 7,951,711 B2 | 5/2011 | Dussarrat |
| 8,012,536 B2 | 9/2011 | Shenai-Khatkhate et al. |
| 8,053,365 B2 | 11/2011 | Humayun et al. |
| 8,153,831 B2 | 4/2012 | Thompson et al. |
| 8,367,546 B2 | 2/2013 | Humayun et al. |
| 8,553,466 B2 | 10/2013 | Han et al. |
| 8,559,235 B2 | 10/2013 | Yoon et al. |
| 8,654,587 B2 | 2/2014 | Yoon et al. |
| 9,034,760 B2 | 5/2015 | Chen et al. |
| 9,034,768 B2 | 5/2015 | Chandrashekar et al. |
| 9,070,749 B2 | 6/2015 | Kang |
| 9,175,023 B2 | 11/2015 | Odedra et al. |
| 2002/0182320 A1* | 12/2002 | Leskela .......... C23C 16/34 427/250 |
| 2006/0046478 A1 | 3/2006 | Lim |
| 2006/0068103 A1 | 3/2006 | Machida et al. |
| 2009/0022891 A1 | 1/2009 | Sakai et al. |
| 2011/0233648 A1 | 9/2011 | Seol et al. |
| 2013/0196065 A1 | 8/2013 | Heys et al. |
| 2015/0176120 A1 | 6/2015 | Lansalot-Matras et al. |

FOREIGN PATENT DOCUMENTS

| | | |
|---|---|---|
| JP | 2012184449 A | 9/2012 |
| KR | 100614993 B | 8/2006 |
| KR | 101306810 B | 9/2013 |
| KR | 101306811 B | 9/2013 |
| KR | 101306812 B | 9/2013 |
| KR | 101532995 B | 6/2015 |
| KR | 101546319 B | 8/2015 |
| WO | WO-2012118200 A | 9/2012 |

* cited by examiner

ORGANOMETALLIC PRECURSORS, METHODS OF FORMING A LAYER USING THE SAME AND METHODS OF MANUFACTURING SEMICONDUCTOR DEVICES USING THE SAME

CROSS-REFERENCE TO RELATED APPLICATION

This application claims priority under 35 USC § 119 to Korean Patent Application No. 10-2016-0129937, filed on Oct. 7, 2016 in the Korean Intellectual Property Office (KIPO), the contents of which are incorporated by reference herein in their entirety.

BACKGROUND

1. Field

Example embodiments relate to organometallic precursors, methods of forming a layer using the same and methods of manufacturing semiconductor devices using the same. More particularly, example embodiments relate to organometallic precursors including a central metal and an organic ligand, methods of forming a layer using the same and methods of manufacturing semiconductor devices using the same.

2. Description of Related Art

A thin film including a metal nitride such as tungsten nitride may be used for forming a wiring structure of a semiconductor device, such a gate electrode, a wiring, a contact or the like. In order to form a metal nitride thin film, a vapor deposition process using a metal precursor and a nitrogen-containing reaction gas may be performed.

The metal precursor may react with the nitrogen-containing reaction gas to generate a byproduct, which may damage a structure of the semiconductor device.

SUMMARY

Example embodiments provide organometallic precursors having improved physical and chemical properties.

Example embodiments provide methods of forming a layer using the organometallic precursors.

Example embodiments provide methods of manufacturing a semiconductor device using the organometallic precursors.

According to example embodiments, an organometallic precursor includes a central metal that is tungsten, a cyclopentadienyl ligand bonded to the central metal, and a first structure or a second structure. The first structure includes an alkylsilyl group bonded to the cylcopentadienyl ligand. The second structure includes an allyl ligand bonded to the central metal.

According to example embodiments, a method of manufacturing a semiconductor device includes forming a barrier conductive layer by providing an organometallic precursor is provided on a semiconductor substrate, and forming a metal layer on the barrier conductive layer. The organometallic precursor includes tungsten as a central metal and a cyclopentadienyl ligand bonded to the central metal. The organometallic precursor includes a first structure or a second structure. The first structure includes an alkylsilyl group bonded to the cylcopentadienyl ligand. The second structure includes an allyl ligand bonded to the central metal.

According to example embodiments, a method of forming a layer includes forming a precursor thin film on a substrate, forming a metal nitride layer by providing a reaction gas over the precursor thin film, and forming a plurality of metal nitride layers by repeating the forming the precursor thin film and the forming the metal nitride layer at least one time. The precursor thin film includes an organometallic precursor. The organometallic precursor includes a cyclopentadienyl ligand bonded to a central metal and one of a first structure and a second structure. The first structure includes an alkylsilyl group bonded to the cyclopentadienyl ligand and the second structure includes an allyl ligand bonded to the central metal. The reaction gas includes a nitrogen-containing gas.

In example embodiments, an organometallic precursor may limit and/or prevent generation of a byproduct containing halogen such as fluorine. Thus, damage to peripheral structures may be limited (and/or prevented). Furthermore, a metal layer and/or a metal nitride layer, which is thermally and chemically stable, may be obtained.

BRIEF DESCRIPTION OF THE DRAWINGS

Example embodiments will be more clearly understood from the following detailed description taken in conjunction with the accompanying drawings.

FIG. 1 a flow chart explaining a method of forming a layer according to some example embodiments.

FIGS. 2 to 7 are cross-sectional views illustrating a method of forming a layer according to some example embodiments.

FIGS. 8 to 10 are cross-sectional views illustrating a method of forming a layer according to some example embodiments.

FIGS. 11 to 15 are cross-sectional views illustrating a method of manufacturing a semiconductor device according to some example embodiments.

FIGS. 16 to 19 are cross-sectional views illustrating a method of manufacturing a semiconductor device according to some example embodiments.

FIGS. 20 to 26 are cross-sectional views illustrating a method of manufacturing a semiconductor device according to some example embodiments.

DETAILED DESCRIPTION

Figure 1:
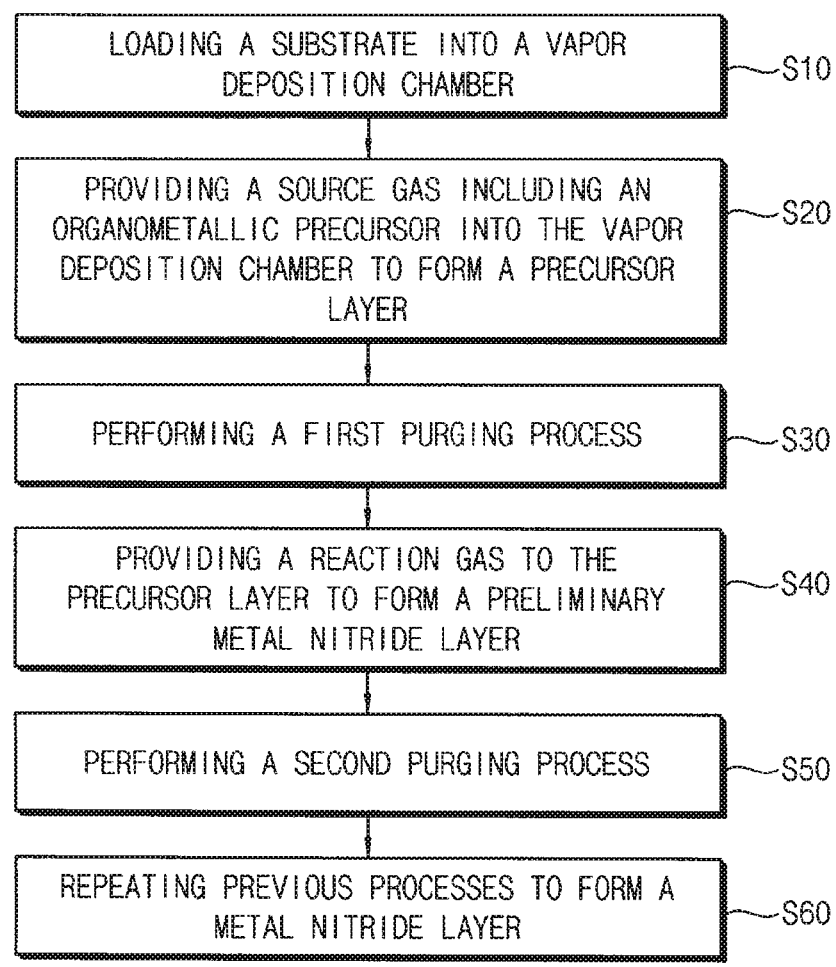
FIGS. 1 to 26 represent non-limiting, example embodiments as described herein.

Various example embodiments will be described more fully hereinafter with reference to the accompanying drawings, in which some example embodiments are shown.

Organometallic Precursor

An organometallic precursor according to some example embodiments includes tungsten (W) as a central metal, and ligands bonded to the central metal. For example, the ligands may be bonded to the central metal with coordinate covalent interaction. At least one of the ligands may include a cyclopentadienyl (Cp) ligand. The cyclopentadienyl ligand may be stably bonded to the central metal by a resonance structure to have improved thermal stability. Thus, a thin film including tungsten or tungsten nitride (WNx) may be formed with high reliability.

In some example embodiments, the cyclopentadienyl ligand of the organometallic precursor may be bonded to an alkylsilyl group. Thus, thermal stability of the cyclopentadienyl ligand in a vapor deposition process may be further improved.

For example, three alkyl groups may be bonded to a silicon atom in the alkylsilyl group to increase thermal stability.

In some example embodiments, the ligands of the organometallic precursor may further include a carbonyl (—C=O) ligand for ease of ligand separation.

For example, the organometallic precursor may be represented by the following Chemical Formula 1.

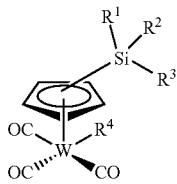

[Chemical Formula 1]

In Chemical Formula 1, R1, R2, R3 and R4 may be independently a hydrogen atom, a halogen atom or an alkyl group of C1 to C7.

For example, the organometallic precursor may be represented by the following Chemical Formulas 1-1, 1-2, 1-3 or 1-4.

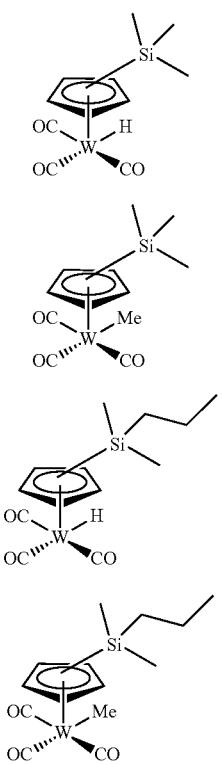

[Chemical Formula 1-1]

[Chemical Formula 1-2]

[Chemical Formula 1-3]

[Chemical Formula 1-4]

In some example embodiments, (dimethylpropylsilyl cyclopentadienyl)methyl(tricarbonyl)tungsten represented by Chemical Formula 1-4 may be used for the organometallic precursor.

In some example embodiments, the organometallic precursor may further include an allyl ligand bonded to the cyclopentadienyl ligand.

In some example embodiments, the ligands of the organometallic precursor may further include a carbonyl (—C=O) ligand for ease of ligand separation.

For example, the organometallic precursor may be represented by the following Chemical Formula 2.

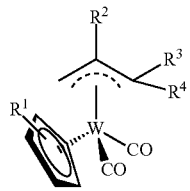

[Chemical Formula 2]

In Chemical Formula 2, R1, R2, R3 and R4 may be independently a hydrogen atom, a halogen atom or an alkyl group of C1 to C7.

As represented by the Chemical Formula 2, the allyl ligand may be bonded to tungsten with coordinate covalent interaction to form a resonance structure. Thus, thermal stability of the organometallic precursor may be further increased.

For example, (ethyl cyclopentadienyl)(2-methylallyl)(dicarbonyl)tungsten represented by Chemical Formula 1-4 may be used for the organometallic precursor.

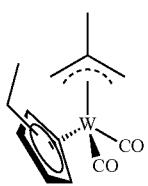

[Chemical Formula 2-1]

The term of "alkyl" used in the Chemical Formulas 1 and 2 may represent a linear or branched saturated hydrocarbon group. For example, the alkyl group may include a methyl group, an ethyl group, an isobutyl group, a pentyl group, a hexyl group or the like. For example, at least one carbon atom in the alkyl group of C1 to C7 may be bonded to a substituent group, and the number of carbon atoms of the substituent group is not included in or not counted for carbon atoms of the alkyl group.

In some example embodiments, the organometallic precursors represented by Chemical Formulas 1 and 2 may be used each alone or in a combination thereof. For example, combination of at least two of the compounds represented by Chemical Formulas 1 and 2 may be used for the organometallic precursors.

The organometallic precursors have a relatively low melting temperature. Thus, the organometallic precursors may have increased volatility. Thus, the organometallic precursors may be easily used for a source gas in a vapor deposition process such as a chemical vapor deposition (CVD) process, an atomic layer deposition (ALD) process or the like. Furthermore, since the organometallic precursors have increased thermal stability, the organometallic precursors may be limited (and/or prevented) from being decomposed by heat before adhering to or being adsorbed onto an object. Thus, a tungsten-containing thin film having fewer defects and having superior electrical and mechanical properties may be formed.

The tungsten-containing thin film may include tungsten, tungsten nitride, tungsten carbide, tungsten carbonitride or the like.

Hereinafter, methods of forming a layer and methods of manufacturing a semiconductor device using the organometallic precursors according to some example embodiments will be explained.

FIG. 1 is a flow chart explaining a method of forming a layer according to some example embodiments. FIGS. 2 to 7 are cross-sectional views illustrating a method of forming a layer according to some example embodiments.

Figure 2:
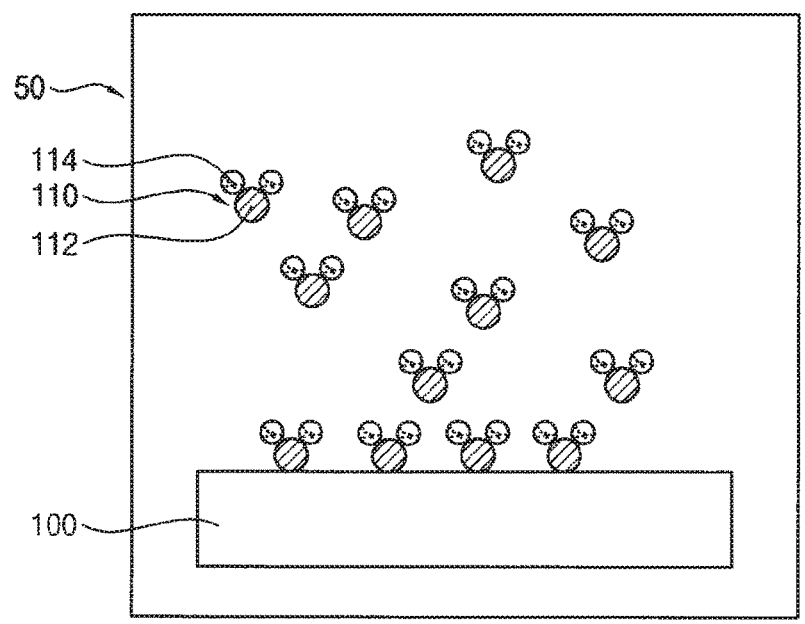

Referring to FIGS. 1 and 2, in operation S10, a substrate 100 may be loaded in a vapor deposition chamber 50.

According to some example embodiments, the vapor deposition chamber 50 may be used for an ALD process. The vapor deposition chamber 50 may include a susceptor on which the substrate 100 is loaded. A plurality of substrates 100 may be disposed horizontally on the susceptor. While the susceptor is rotated, for example, a tungsten-containing thin film may be formed on each of the substrates 100. For example, the vapor deposition chamber 50 may be a single wafer type chamber.

The vapor deposition chamber 50 may include at least one flow channel. For example, the vapor deposition chamber 50 may include a first flow channel through which a source gas including an organometallic precursor is provided, and a second flow channel through which a reaction gas is provided. The vapor deposition chamber 50 may further include a third flow channel through which a purging gas is provided.

The substrate 100 may be an object on which the tungsten-containing thin film is formed. For example, the substrate 100 may be formed from a semiconductor wafer such as a silicon wafer or a germanium wafer.

Even though not illustrated, various structures may be further formed on the substrate 100. For example, a conductive layer including a metal, a metal nitride, a metal silicide, a metal oxide or the like, an electrode, or an insulation layer including silicon oxide or silicon nitride may be further formed. In some example embodiments, an insulation layer including a hole or an opening therein may be formed on the substrate 100, and the tungsten-containing thin film may be vapor-deposited in the hole or the opening through subsequent processes.

Figure 3:
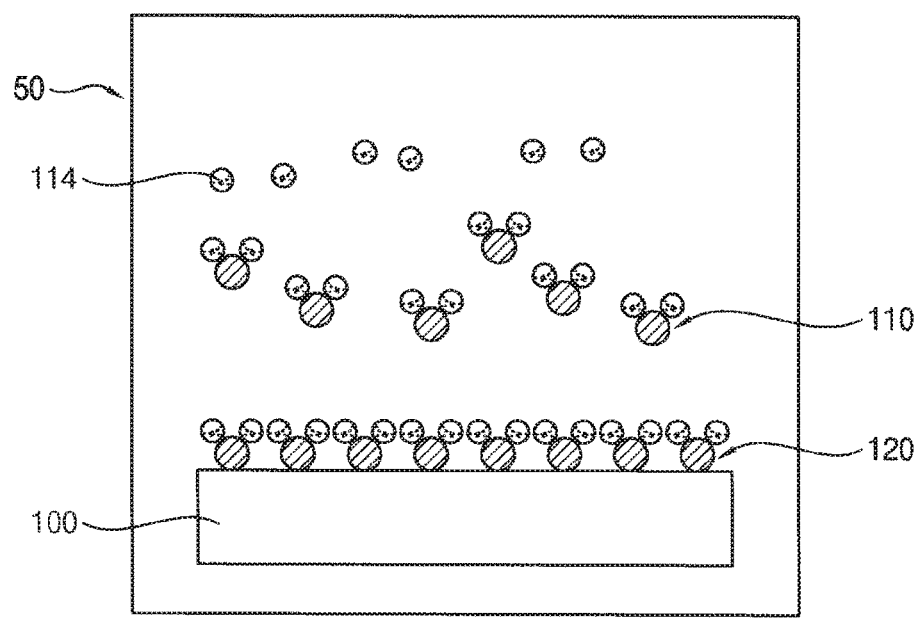

Referring to FIGS. 1, 2 and 3, in operation S20, a source gas including an organometallic precursor 110 may be provided into the vapor deposition chamber 50 to form a precursor thin film 120 on the substrate 100, for example.

For example, the organometallic precursor 110 may be vaporized by a bubbler so that the source gas may be provided into the vapor deposition chamber 50.

The organometallic precursor 110 may include ligands 114 bonded to a central metal 112. As previously explained, the organometallic precursor 110 may include tungsten as the central metal 112. At least one of the ligands 114 may include a cyclopentadienyl ligand. In some example embodiments, the ligands 114 may further include an allyl ligand. The cyclopentadienyl ligand may be further bonded to an alkylsilyl group.

In some example embodiments, the organometallic precursor 110 may at least one of compounds represented by Chemical Formula 1 or 2.

FIG. 2 shows that two ligands 114 are bonded to the central metal 112, however, example embodiments are not limited thereto, and the organometallic precursor 110 may include at least three ligands.

The organometallic precursor 110 according to some example embodiments has a relatively low melting temperature. Thus, the organometallic precursor 110 may be easily vaporized and provided into the vapor deposition chamber 50. The organometallic precursor 110 or the source gas may be provided into the vapor deposition chamber 50 by a carrier gas. For example, the carrier gas may include an inactive gas such as argon (Ar), helium (He), krypton (Kr), xenon (Xe) or the like.

A temperature of the vapor deposition chamber 50 may be maintained in a range of about 200° C. to about 600° C. When the temperature of the vapor deposition chamber 50 is less than 200° C., a chemical adsorption between the organometallic precursor 110 and the substrate 100 may not be sufficient. When the temperature of the vapor deposition chamber 50 is more than 600° C., the precursor thin film 120 may be crystallized or damaged. In some example embodiments, a temperature of the vapor deposition chamber 50 may be maintained in a range of about 200° C. to about 400° C.

As illustrated in FIG. 2, the organometallic precursor 110 may be chemically adsorbed onto a surface of the substrate 100 to form the precursor thin film 120 illustrated in FIG. 3.

The organometallic precursor 110 may have increased thermal stability, for example, in the temperature range of the vapor deposition chamber 50. Thus, the ligand 114 may be limited (and/or prevented) from being decomposed by heat before the organometallic precursor 110 is chemically adsorbed onto the surface of the substrate 100. When the organometallic precursor 110 is decomposed by heat before adhering to the substrate 100, impurities generated from the organometallic precursor 110 may hinder diffusion of the organometallic precursor 110 on the surface of the substrate 100. Thus, step coverage of the precursor thin film 120 or the tungsten-containing thin film may be limited and/or deteriorated.

However, the organometallic precursor 110 according to some example embodiments has high volatility and increase thermal stability. Thus, the precursor thin film 120 or the tungsten-containing thin film, which has superior step coverage and high reliability, may be formed.

As illustrated in FIG. 3, organometallic precursors 110, which does not adhere to the surface of the substrate 100, may drift in the vapor deposition chamber 50. Furthermore, ligands 114 separated from some organometallic precursors 110 may drift therewith in the vapor deposition chamber 50.

Figure 4:
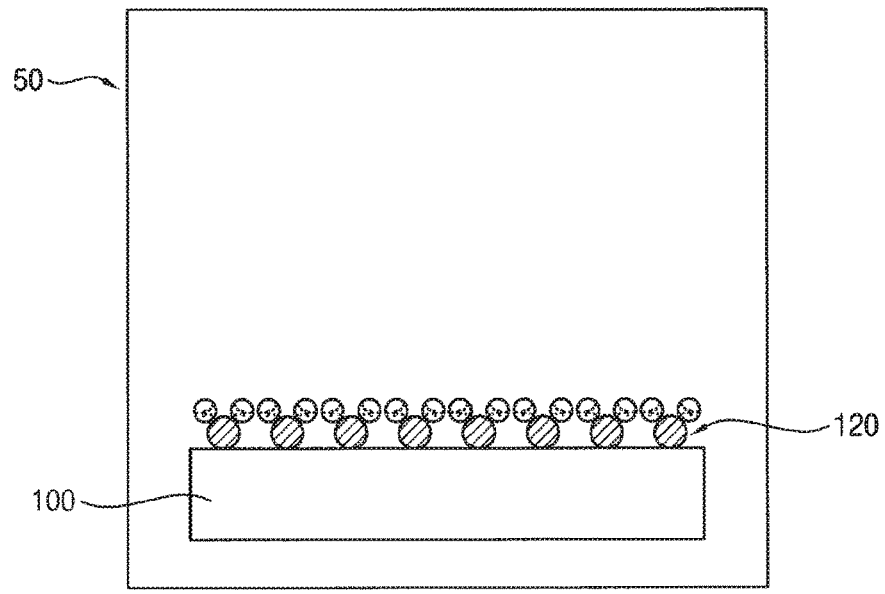

Referring to FIGS. 1 and 4, in operation S30, a first purging process may be performed.

Through the first purging process, organometallic precursors 110, which physically adhere to or does not adhere to the surface of the substrate 100 as illustrated in FIG. 3, may be discharged or removed from the vapor deposition chamber 50. Furthermore, the ligands 114 drifting in the vapor deposition chamber 50 may be discharged or removed therewith. For example, a first purging gas used in the first purging process may include an Ar gas.

Through the first purging process, impurities drifting in the vapor deposition chamber 50 may be removed, and the precursor thin film 120 may remain on the substrate 100.

Figure 5:
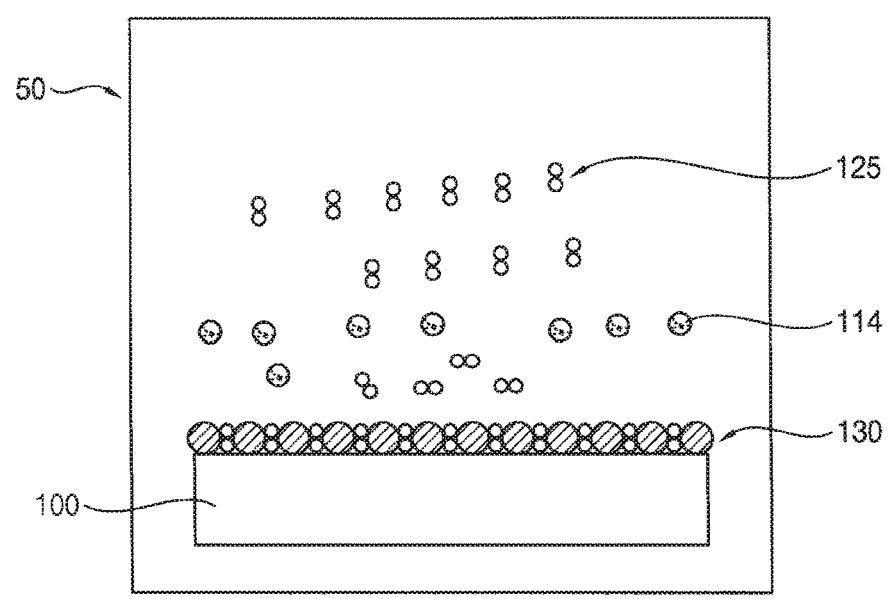

Referring to FIGS. 1 and 5, in operation S40, a reaction gas including a reaction material 125 is provided into the vapor deposition chamber 50 to change the precursor thin film 120 into a preliminary metal nitride layer 130.

The reaction gas may include a nitrogen-containing gas. In some example embodiments, the nitrogen-containing gas may include ammonia ($NH_3$). In some example embodiments, the nitrogen-containing gas may include nitrogen dioxide ($NO_2$) and/or nitrous oxide ($N_2O$).

FIG. 5 shows that the reaction material 125 has two atoms, however, example embodiments are not limited thereto, and the reaction material 125 may have at least three atoms.

The ligands 114 may be substituted with nitrogen atoms included in the reaction material 125. Thus, the ligands 114 separated from the precursor thin film 120 may drift in the vapor deposition chamber 50.

In some example embodiments, the nitrogen atoms may be inserted between central metals, which may be tungsten atoms, to form a preliminary metal nitride layer 130 having a substantially atomic layer, as illustrated in FIG. 5.

Figure 6:
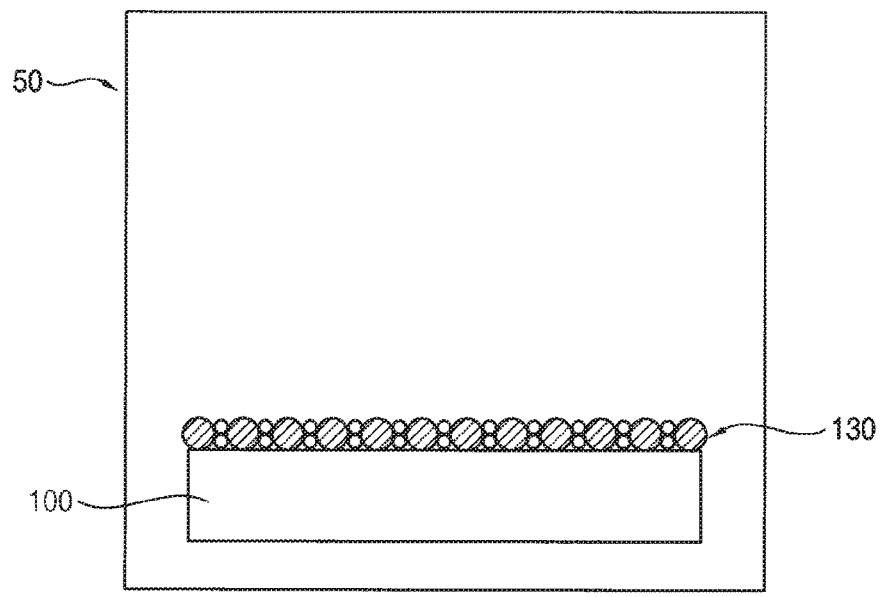
Figure 7:
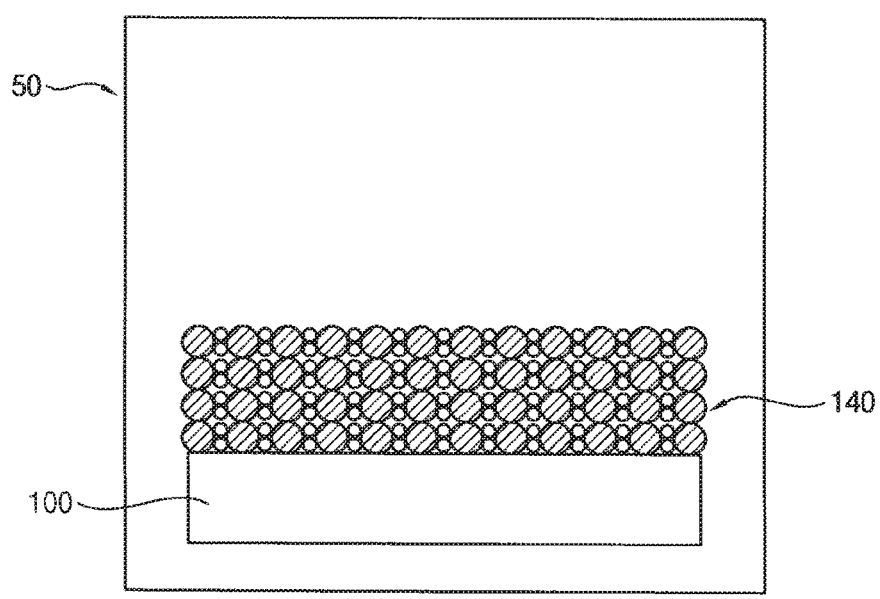

Referring to FIGS. 1 and 6, in operation S50, a second purging process may be performed. The reaction material 125 remaining in the vapor deposition chamber 50 and the ligands 114 substituted with the reaction material 125 may be discharged or removed from the vapor deposition chamber 50.

Referring to FIGS. 1 to 7, operations S20 to S50 may be repeated with a plurality of cycles, for example, in operation S60. Thus, a plurality of preliminary metal nitride layers 130 may be sequentially deposited to form a metal nitride layer 140.

As previously explained, a metal nitride layer 140 having superior step coverage and mechanical properties may be formed by using the organometallic precursor 110 having increased thermal stability and volatility according to some example embodiments.

As a comparative example, a metal halide such as WF6 may be used to form a metal nitride layer. The metal halide may react with a reaction gas such as ammonia to form a metal nitride layer. However, a reactive byproduct such as HF may be generated, and the reactive byproduct may etch other structures including silicon oxide or silicon. Thus, reliability and yield of a manufacturing process for a semiconductor device may be reduced.

In contrast, the organometallic precursors according to some example embodiments do not contain halogen, or may have lower halogen amount with compared to the metal halide. For example, the organometallic precursors may contain a small amount of halogen such that other structures are not substantially damaged. Thus, a metal nitride layer having higher reliability may be formed without a reactive byproduct.

In some example embodiments explained with reference to FIGS. 1 to 7, the organometallic precursor is used to form a metal nitride layer. However, a metal layer such as a tungsten layer may be formed depending on a reaction gas. Furthermore, a metal carbide layer including tungsten carbide or tungsten carbonitride may be formed depending on an amount of carbon in the organometallic precursor.

Figure 8:
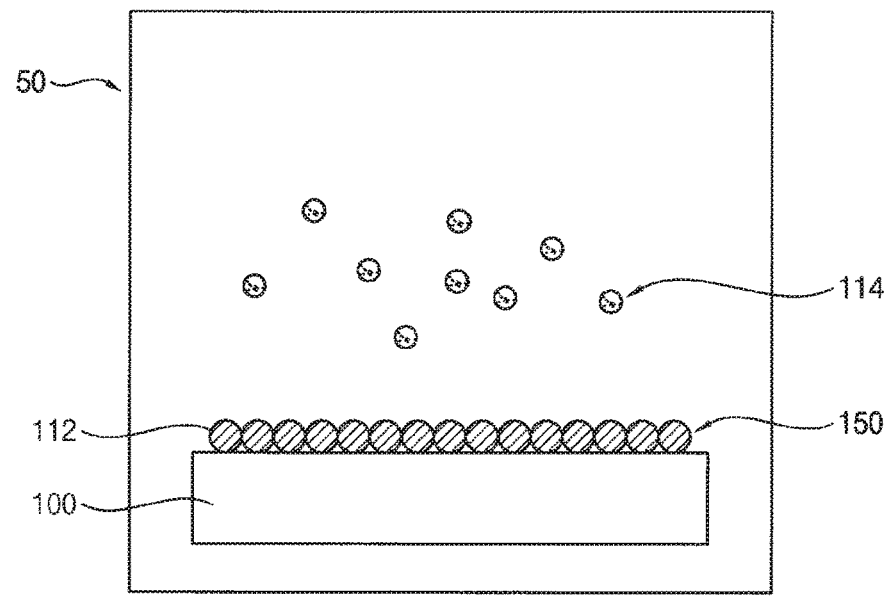
Figure 9:
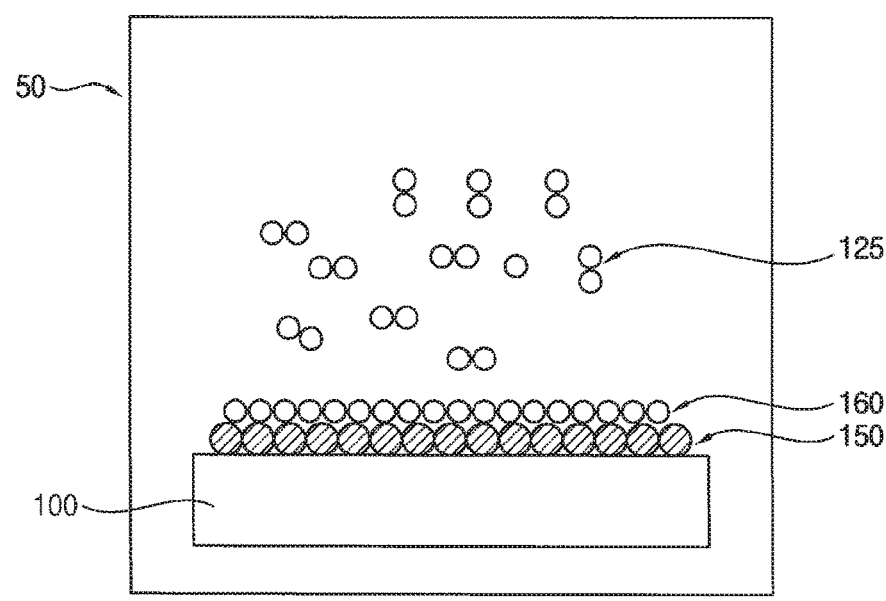
Figure 10:
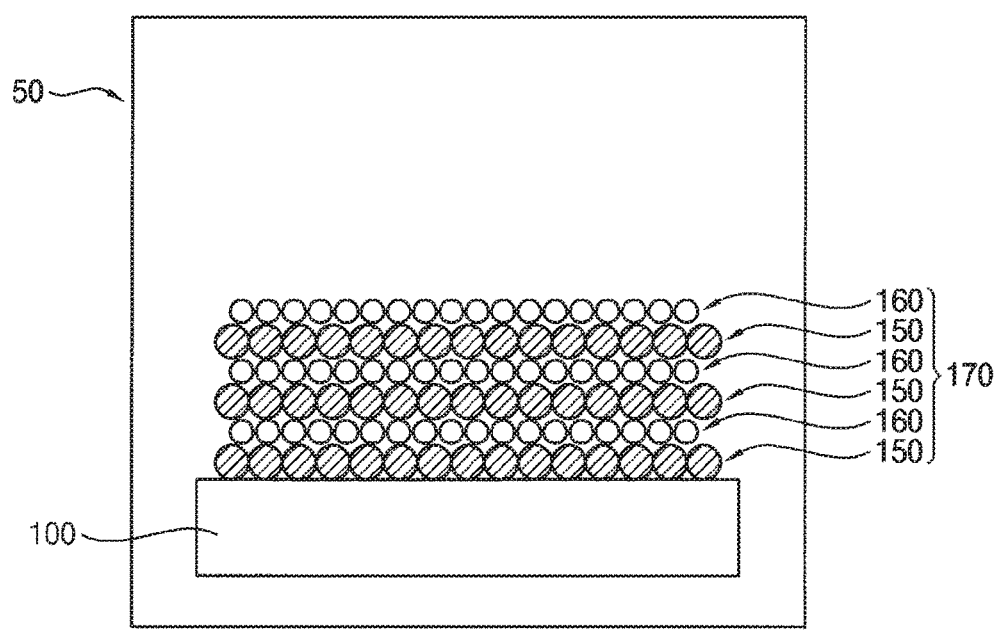

FIGS. 8 to 10 are cross-sectional views illustrating a method of forming a layer according to some example embodiments. Hereinafter, any process or any material, which is same or similar to those previously explained with reference to FIGS. 1 to 7, may be omitted.

Referring to FIG. 8, an organometallic precursor may be provided to a substrate 100 loaded in a vapor deposition chamber 50 to form a metal atomic layer 150.

As previously explained with reference to FIG. 3, the organometallic precursor may include a central metal 112, for example, such as tungsten, and ligands 114 bonded to the central metal 112. The organometallic precursor may be chemically adsorbed onto a surface of the substrate 100.

According to some example embodiments, the ligands 114 may be separated from the organometallic precursor chemically adsorbed onto the substrate 100 through a first purging process. For example, a flow amount of a first purging gas used for the first purging process, and a temperature in a vapor deposition chamber 50 may be adjusted to remove the ligands 114 separated from the organometallic precursor, and the organometallic precursor drifting in the vapor deposition chamber 50.

As a result, a metal atomic layer 150 substantially consisting of central metals 112 may be formed on the surface of the substrate 100. For example, the metal atomic layer 112 may be substantially a tungsten atomic layer.

Referring to FIG. 9, a reaction gas including a reaction material 125 may be provided to the metal atomic layer 150 in the vapor deposition chamber 50. As previously explained, the reaction gas may include a nitrogen-containing gas such as ammonia. Thus, the metal atomic layer 150 may react with the reaction gas to form a reaction material layer 160. In some example embodiments, the reaction material layer 160 may be a nitrogen atomic layer.

Thereafter, the reaction material 125 remaining in the vapor deposition chamber 50 may be discharged or removed through a second purging process.

Referring to FIG. 10, the processes previously explained with reference to FIGS. 8 and 9 may be repeated with a plurality of cycles.

In some example embodiments, the metal atomic layer 150 and the reaction material layer 160 may be alternately deposited to form a metal nitride layer 170.

FIGS. 11 to 15 are cross-sectional views illustrating a method of manufacturing a semiconductor device according to some example embodiments. For example, FIGS. 11 to 15 may illustrate a method of forming a conductive structure of a semiconductor device using an organometallic precursor according to some example embodiments.

Figure 11:
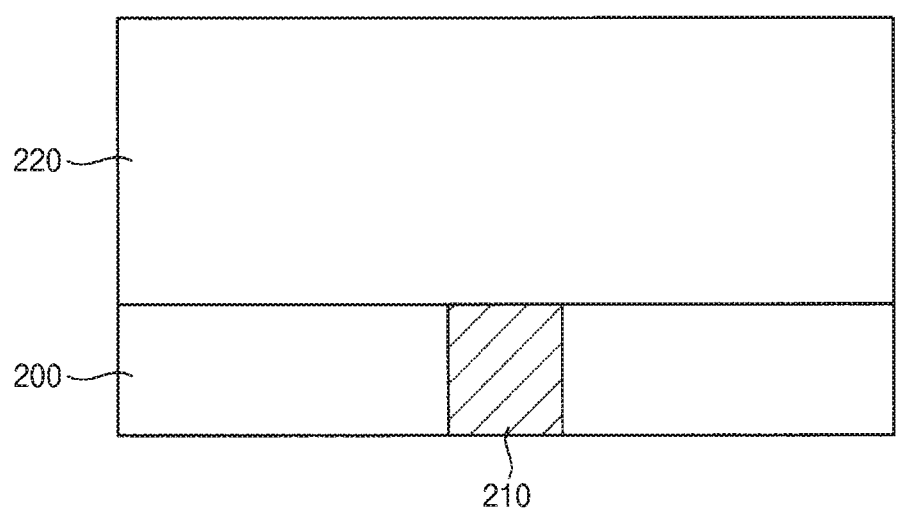

Referring to FIG. 11, an interlayer insulation layer 220 may be formed on a lower structure 200 including a conductive pattern 210 formed therein.

In some example embodiments, the lower structure 200 may include a lower insulation layer formed on the substrate 100 illustrated in FIG. 2. A circuit element including a word line, a gate structure, a diode, a source/drain layer, a contact, a wiring or the like may be formed on the substrate 100.

The lower structure 200 may be formed on the substrate 100 to cover the circuit element. The conductive pattern 210 may be formed in the lower structure 200. The conductive pattern 210 may function as a plug to be electrically connected to at least a portion of the circuit element.

For example, the lower structure 200 may be formed through a CVD process to include a silicon-oxide-based material such as plasma enhanced oxide (PEOX), tetraethyl orthosilicate (TEOS) or silicate glass. The conductive pattern 210 may include a metal such as tungsten (W), copper (Cu), titanium (Ti), tantalum (Ta) or the like, metal nitride, metal silicide and or polysilicon doped with impurities.

In some example embodiments, the lower structure 200 may include a semiconductor substrate. For example, the lower structure 200 may include silicon, germanium, silicon-germanium or a III-V group compound such as GaP, GaAs, GaSb or the like. In some example embodiments, the lower structure 200 may include a silicon-on-insulator (SOI) substrate or a germanium-on-insulator (GOI) substrate. The conductive pattern 210 may be an impurity region of n-type or p-type, which is formed in the lower structure 200.

The interlayer insulation layer 220 may include the silicon-oxide-based material or a low dielectric organic oxide such as polysiloxane, silsesquioxane or the like. For example, the interlayer insulation layer 220 may be formed through a CVD process or a spin coating process.

Figure 12:
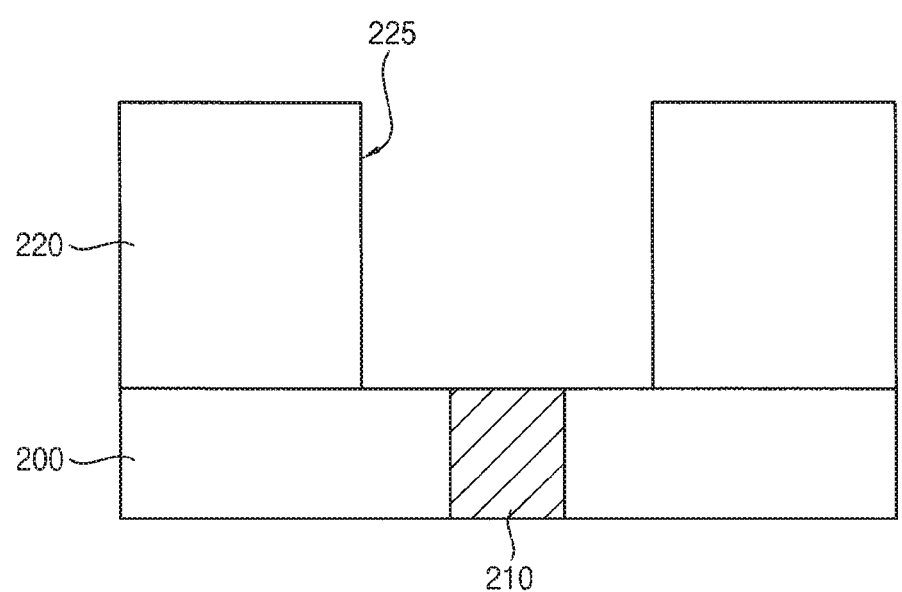

Referring to FIG. 12, the interlayer insulation layer 220 may be partially removed to form an opening 225 partially exposing at least a portion of the conductive pattern 210.

In some example embodiments, the opening 225 may have a shape of a hole entirely exposing an upper surface of the conductive pattern 210. In some example embodiments, the opening 225 having a shape of a trench exposing the upper surface of the conductive pattern 210 and linearly extending.

Figure 13:
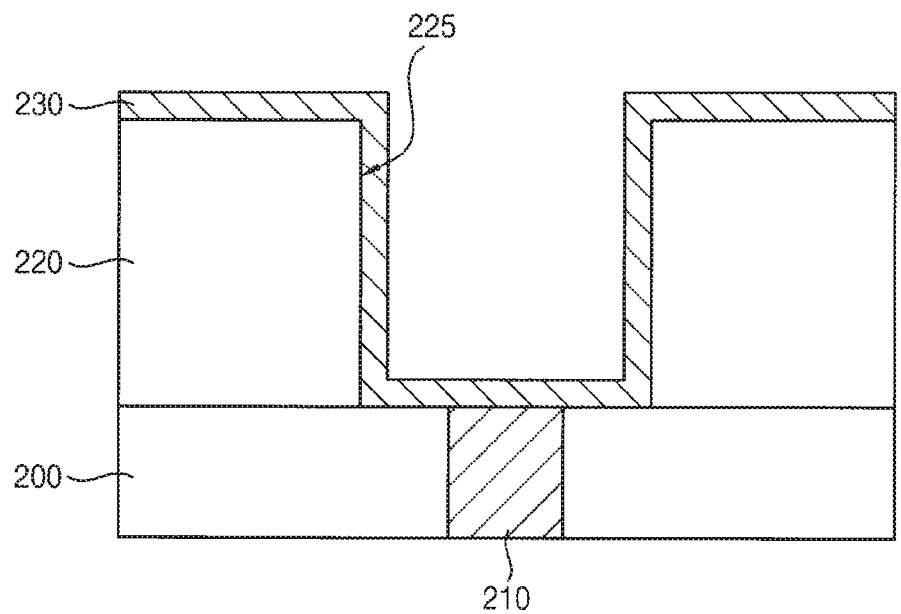

Referring to FIG. 13, a barrier conductive layer 230 may be formed along a surface of the interlayer insulation layer 220 and a sidewall and a bottom surface of the opening 225.

In some example embodiments, the barrier conductive layer 230 may be formed by the method of forming a layer, which is previously explained with reference to FIGS. 1 to 7 or FIGS. 8 to 10, using an organometallic precursor according to some example embodiments.

As previously explained, the organometallic precursor may include tungsten as a central metal, and a cyclopentadienyl ligand bonded to tungsten. The organometallic precursor may further include an allyl ligand. An alkylsilyl ligand may be further bonded to the cyclopentadienyl ligand.

In some example embodiments, the organometallic precursor may include at least one of compounds represented by Chemical Formulas 1 or 2.

The barrier conductive layer 230 may be formed through an ALD process or a plasma enhanced ALD (PEALD) process, which is explained with reference to FIGS. 1 to 7 or FIGS. 8 to 10, using the organometallic precursor. The organometallic precursor has increased thermal stability and volatility. Thus, the barrier conductive layer 230 may have a substantially uniform thickness on an entire surface of the opening 225.

In some example embodiments, the barrier conductive layer 230 may be formed through a CVD process including a plasma enhanced CVD (PECVD) process, a low pressure CVD (LPCVD) process, a high density plasma CVD (HDP-CVD) process or the like.

In some example embodiments, the barrier conductive layer 230 may include tungsten nitride. In some example embodiments, the barrier conductive layer 230 may include tungsten carbide or tungsten carbonitride.

Figure 14:
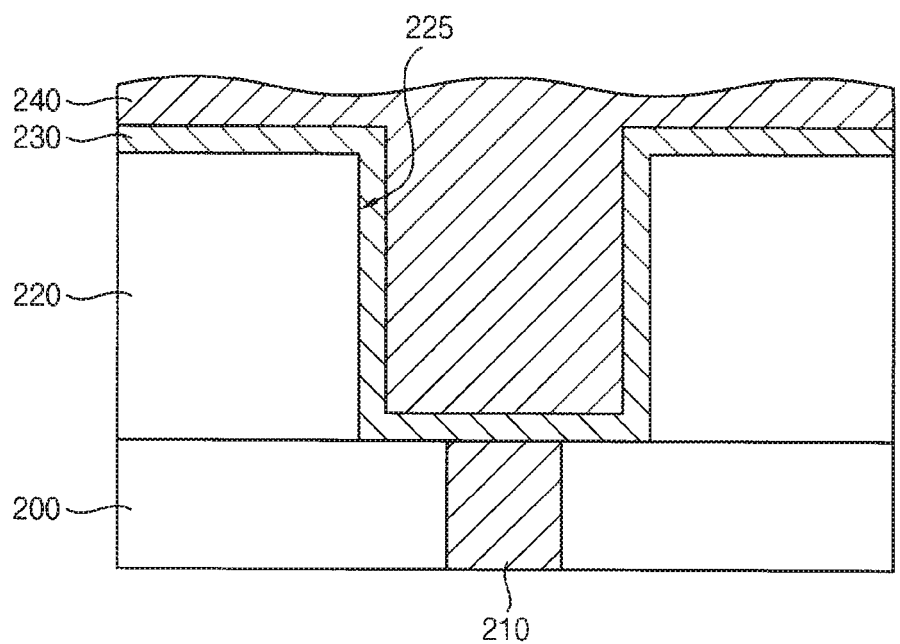

Referring to FIG. 14, a metal layer 240 sufficiently filling the opening 225 may be formed on the barrier conductive layer 230. The metal layer 240 may include a metal such as tungsten, aluminum, copper, titanium, tantalum or the like, and may be formed through an ALD process, a sputtering process or a CVD process.

In some example embodiments, the metal layer 240 may be formed by using the organometallic precursor according to some example embodiments. For example, providing the organometallic precursor and the purging process may be repeated to form the metal layer 240 having a structure having tungsten atomic layers that are vertically deposited. In some example embodiments, hydrogen ($H_2$) gas may be used as a reaction gas instead of the nitrogen-containing gas.

In some example embodiments, the barrier conductive layer 230 and the metal layer 240 may be deposited with in-situ in a substantially same vapor deposition chamber.

Figure 15:
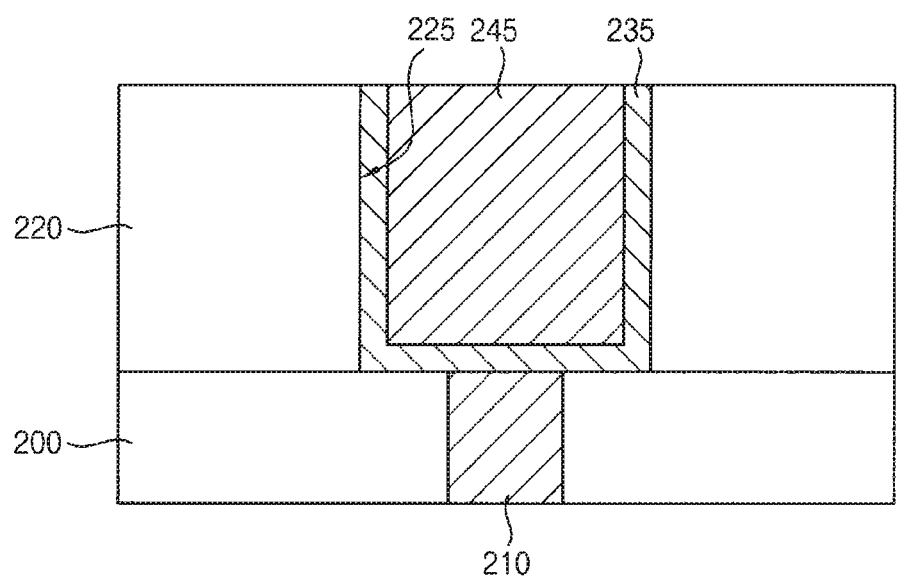

Referring to FIG. 15, an upper portion of the metal layer 240 and the barrier conductive layer 230 may be planarized, for example, by a chemical mechanical polishing (CMP) process until an upper surface of the interlayer insulation layer 220 is exposed.

A conductive structure electrically connected to the conductive pattern 210 and including a barrier conductive pattern 235 and a metal filling pattern 245 may be formed in the opening 225 through the above planarizing process. In some example embodiments, the conductive structure may include a deposition structure of tungsten nitride/tungsten ($WN_x/W$).

In some example embodiments, the conductive structure may be provided as a contact electrically connected, for example, to the impurity region of the semiconductor device. In some example embodiments, the conductive structure may be provided as an upper contact or a wiring, which is electrically connected to a lower contact or a lower plug of the semiconductor device.

FIGS. 16 to 19 are cross-sectional views illustrating a method of manufacturing a semiconductor device according to some example embodiments. For example, FIGS. 16 to 19 may illustrate a method of manufacturing a non-volatile semiconductor device having a planar shape or a 2-dimensional structure.

In FIGS. 16 to 19, two directions that are parallel with an upper surface of a substrate and cross each other are defined as a first direction and a second direction, respectively. For example, the first direction and the second direction may cross each other perpendicularly.

Figure 16:
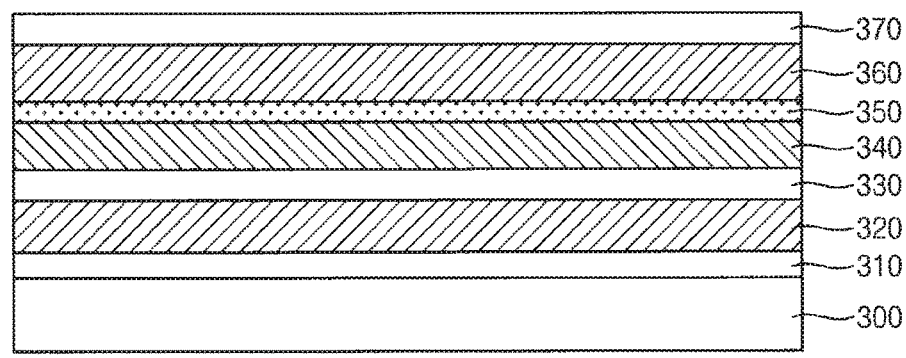

Referring to FIG. 16, a tunnel insulation layer 310, a charge trap layer 320, a dielectric layer 330, a control gate layer 340, a barrier conductive layer 350, a metal gate layer 360 and a gate mask layer 370 may be sequentially formed on a substrate 300.

Examples of the substrate 300 may include a silicon substrate, a germanium substrate, a silicon-germanium substrate, an SOI substrate, a GOI substrate or the like. In some example embodiments, the substrate 300 may include a III-V group compound such as InP, GaP, GaAs, GaSb or the like.

The tunnel insulation layer 310 may include silicon oxide, silicon nitride, silicon oxynitride or the like. In some example embodiments, the tunnel insulation layer 310 may have a deposition structure such as oxide-nitride-oxide (ONO) structure, oxide-silicon-oxide (OSO) structure, oxide-silicon-nitride-oxide (OSNO) structure or the like.

The charge trap layer 320 may be formed through a deposition process, for example, using a silicon precursor and impurities of n-type or p-type. As a result, the charge trap layer 320 may include polysilicon doped with impurities. In some example embodiments, the charge trap layer 320 may be provided as a floating gate layer.

In some example embodiments, after the charge trap layer 320 is formed, the charge trap layer 320, the tunnel insulation layer 310 and an upper portion of the substrate 300 may be partially etched along the first direction to form an element separation trench. The substrate 300 may be divided into an active area and a field area by the element separation trench. Thereafter, an element separation layer that partially fills the element separation trench may be formed. For example, the element separation layer may include silicon oxide. The charge trap layer 320 and the tunnel insulation layer 310 may be changed into a linear pattern extending along the first direction in the active area by the above-explained processes.

Thereafter, the dielectric layer 330, the control gate layer 340, the barrier conductive layer 350 and the metal gate layer 360 and the gate mask layer 370 may be sequentially formed on the charge trap layer 320 and the element separation layer.

For example, the dielectric layer 330 may have a mono-layer structure of an oxide layer or a nitride layer, or a deposition structure such as an ONO structure. In some example embodiments, the dielectric layer 330 may include a metal oxide having a relatively higher permittivity. The control gate layer 340 may include polysilicon doped with impurities.

In some example embodiments, the barrier conductive layer 350 may be formed by the method of forming a layer, which is previously explained with reference to FIGS. 1 to 7 or FIGS. 8 to 10, using an organometallic precursor according to some example embodiments.

As previously explained, the organometallic precursor may include tungsten as a central metal, and a cyclopentadienyl ligand bonded to tungsten. The organometallic precursor may further include an allyl ligand. An alkylsilyl ligand may be further bonded to the cyclopentadienyl ligand. In some example embodiments, the organometallic precursor may include at least one of compounds represented by Chemical Formulas 1 or 2.

The barrier conductive layer 350 may be formed through an ALD process or a plasma enhanced ALD process, which is explained with reference to FIGS. 1 to 7 or FIGS. 8 to 10, using the organometallic precursor.

In some example embodiments, the barrier conductive layer 350 may be formed through a CVD process including a PECVD process, a LPCVD process, a HDP-CVD process or the like.

In some example embodiments, the barrier conductive layer 350 may include tungsten nitride. In some example embodiments, the barrier conductive layer 350 may include tungsten carbide or tungsten carbonitride.

The metal gate layer 360 may include a metal such as tungsten, aluminum, copper, titanium, tantalum or the like, and may be formed through an ALD process, a sputtering process or a CVD process. In some example embodiments, the metal gate layer 360 may be formed by using the organometallic precursor according to some example embodiments.

For example, providing the organometallic precursor and the purging process may be repeated to form the metal gate layer 360 having a structure having tungsten atomic layers that are vertically deposited. In some example embodiments, the barrier conductive layer 350 and the metal gate layer 360 may be deposited with in-situ in a substantially same vapor deposition chamber.

In some example embodiments, the gate mask layer 370 may include silicon nitride or silicon oxynitride.

Figure 17:
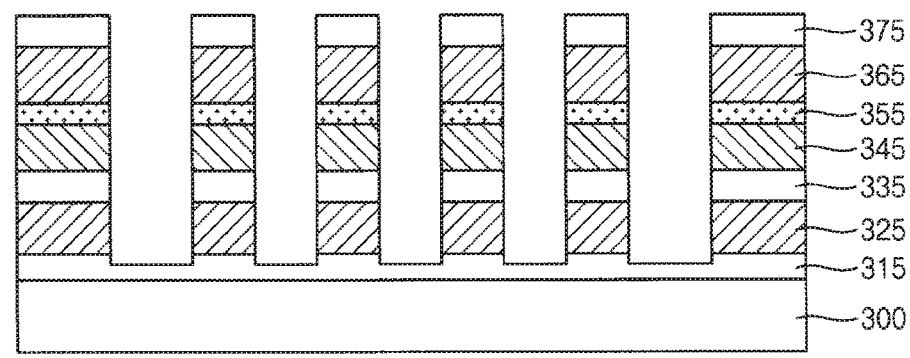

Referring to FIG. 17, the gate mask layer 370 may be partially etched along the second direction to form a plurality of gate masks 375. Thereafter, the metal gate layer 360, the barrier conductive layer 350, the control gate layer 340, the dielectric layer 330, the charge trap layer 320 and the tunnel insulation layer 310 may be sequentially and partially etched by using the gate masks 375 as an etching mask.

As a result, gate structures including a tunnel insulation pattern 315, a charge trap pattern 325, a dielectric pattern 335, a control gate 345, a barrier conductive pattern 355, a metal gate 365 and the gate mask 375, which are sequentially deposited from the upper surface of the substrate 300 may be formed. In some example embodiments, the charge trap pattern 325 may be provided as a floating gate of the gate structure.

A portion of each of the gate structures, for example, which includes the dielectric pattern 335, the control gate 345, the barrier conductive pattern 335, the metal gate 365 and the gate mask 375, may have a linear pattern shape extending along the second direction. In some example embodiments, the charge trap pattern 325 may have an island shape isolated along the first direction and the second direction.

The tunnel insulation pattern 315 may have a linear pattern shape extending along the first direction. The tunnel insulation pattern 315 may be partially removed by the etching process such that the tunnel insulation pattern 315 may be connected between the gate structures that are adjacent to each other along the first direction. As a result, the tunnel insulation pattern 315 may include a recess between the gate structures.

In some example embodiments, a plurality of gate structures may be formed along the first direction. For example, a central portion of the substrate 300 may correspond to a cell area, and gate structures configured to form a memory cell may be formed to have a relatively narrower width with being apart from each other by a relative narrower gap, in the cell area. FIG. 17 shows four gate structures formed in the cell area, however, example embodiments are not limited thereto.

Both peripheral portions of the substrate 300, which interpose the central portion, may correspond to a selection area. Gate structures may be formed to have a relatively larger width with being apart from each other by a relative larger gap, in the selection area than in the cell area.

Figure 18:
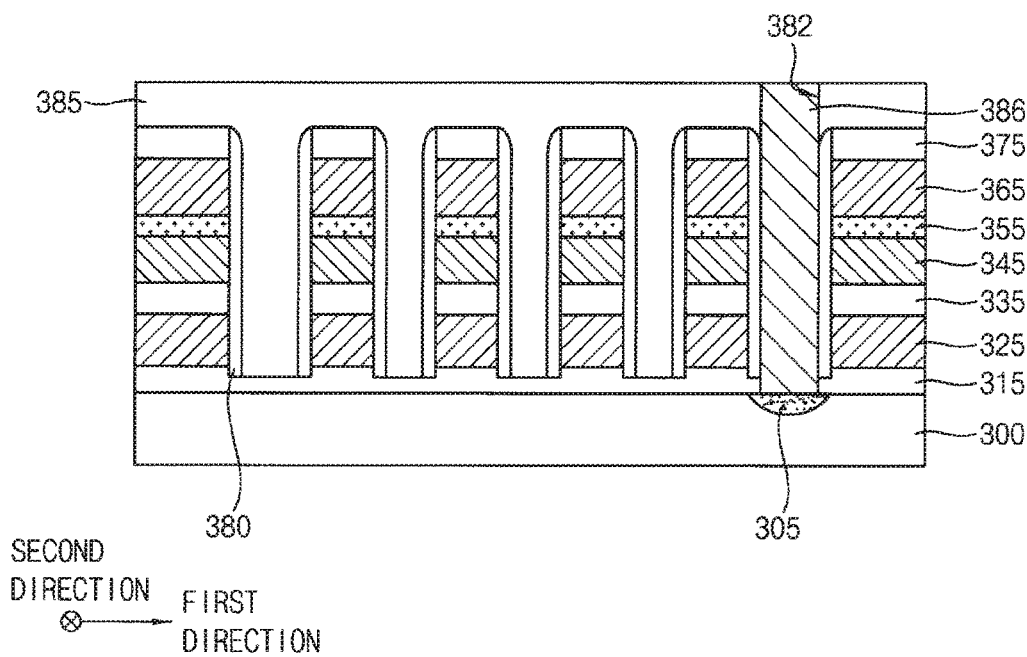

Referring to FIG. 18, a gate spacer 380 may be formed at sidewalls of the gate structures. For example, a spacer layer may be formed along surfaces of the gate structures on the tunnel insulation pattern 315. Thereafter, the spacer layer may be partially removed through an etch-back process or an anisotropic etching process to form the gate spacer 380 on the sidewalls of the gate structures.

For example, the spacer layer may include silicon nitride or silicon oxynitride, and may be formed through an ALD process capable of improving step coverage property.

Thereafter, a first interlayer insulation layer 385 may be formed on the tunnel insulation pattern 315 and the element separation layer to cover the gate structures. For example, the first interlayer insulation layer 385 may be formed through a CVD process, and may include silicon oxide such as PEOX, TEOS or silicate glass.

A first contact 386 may be formed to pass through the first interlayer insulation layer 385. The first contact 386 may contact or be electrically connected to a first impurity region 305.

For example, the first interlayer insulation layer 385 and the tunnel insulation pattern 315 disposed between the cell area and one of the selection areas may be etched to form a first opening. A first impurity may be provided through the first opening to form the first impurity region 305 on the substrate 300. Thereafter, a first conductive layer filling the first opening is formed on the first interlayer insulation layer 385. An upper portion of the first conductive layer may be planarized, for example, through a CMP process to form a first contact 386. The first contact 386 may be provided as a common source line (CSL) or a CSL contact of the semiconductor device.

Figure 19:
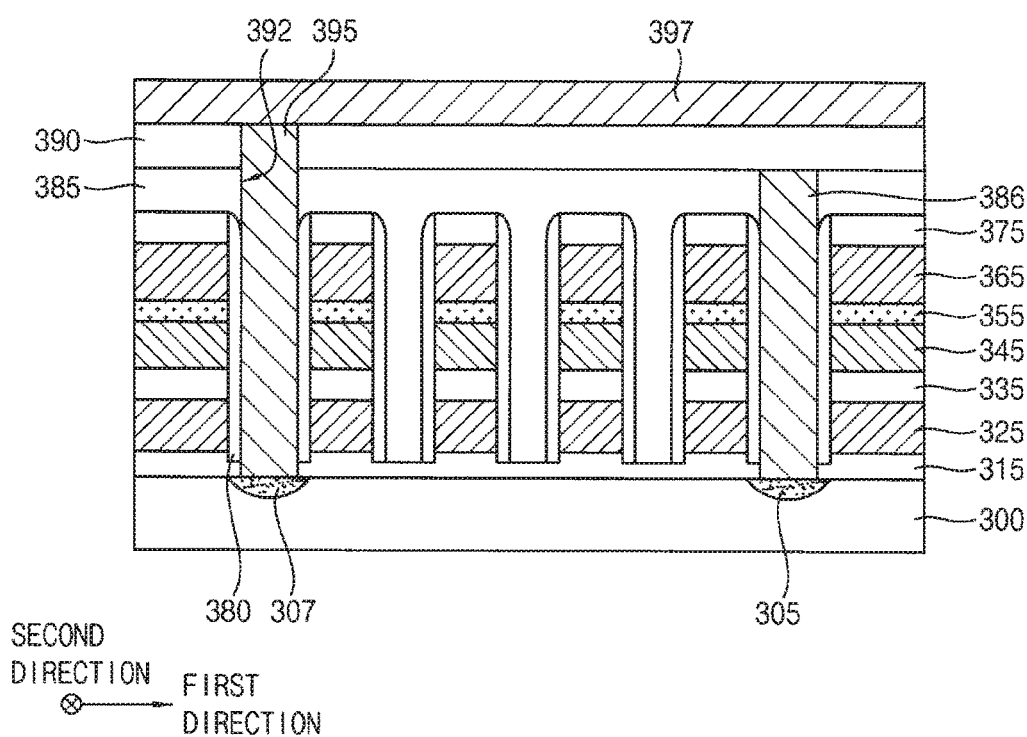

Referring to FIG. 19, a second interlayer insulation layer 390 may be formed to cover the first contact 386 on the first interlayer insulation layer 385. Thereafter, a second opening passing through the second interlayer insulation layer 390, the first interlayer insulation layer 385 and the tunnel insulation pattern 315 may be formed to expose an upper portion of the substrate 300 between the cell area and the other of the selection areas. A second impurity region 305 may be formed on the substrate 300 by impurities provided through the second opening by an ion implantation process.

Thereafter, a second conductive layer filling the second opening may be formed on the second interlayer insulation layer 390. An upper portion of the second conductive layer may be planarized through a CMP process to form a second contact 395.

A third conductive layer may be formed on the second interlayer insulation layer 390 and the second contact 395, and may be patterned to form a bit line 397. For example, the bit line 397 may extend along the first direction. The second contact 395 may be electrically connected to the bit line 397 to function as a bit line contact.

The second interlayer insulation layer 390 may include silicon oxide substantially same as or similar to the first interlayer insulation layer 385. The first to third conductive layers may include a conductive material such as a metal, a metal nitride, a metal silicide, polysilicon doped with impurities or the like, and may be formed through a sputtering process, an ALD process or the like.

In some example embodiments, the first and second contacts 386 and 395 may be formed through processes substantially same as or similar to those previously explained with reference to FIGS. 11 to 15 using an organometallic precursor according to some example embodiments.

In some example embodiments, the first and second contacts 386 and 395 may include tungsten. In some example embodiments, the first and second contacts 386 and 395 may have a deposition structure of tungsten nitride/tungsten.

FIGS. 20 to 26 are cross-sectional views illustrating a method of manufacturing a semiconductor device according to some example embodiments. For example, FIGS. 20 to 26 may illustrate a method of manufacturing a non-volatile semiconductor device having a 3-dimensional structure or a vertical-typed memory device including a vertical channel. In some example embodiments, the vertical-typed memory device may include a three-dimensional memory cell array, which is formed on a substrate in a three-dimensional structure (or a vertical structure). In this case, the memory cell array may include vertical cell strings that are vertically oriented such that at least one memory cell is located over another memory cell. The following patent documents, which are hereby incorporated by reference, describe suitable configurations for three-dimensional memory cell arrays: U.S. Pat. Nos. 7,679,133; 8,553,466; 8,654,587; 8,559,235; and US Pat. Pub. No. 2011/0233648.

In FIGS. 20 to 26, a direction vertically extending from an upper surface of a substrate may be defined as a first direction. Furthermore, two directions that are parallel with the upper surface of the substrate and cross each other may be defined as a second direction and a third direction, respectively. For example, the second direction and third direction may cross each other perpendicularly.

Figure 20:
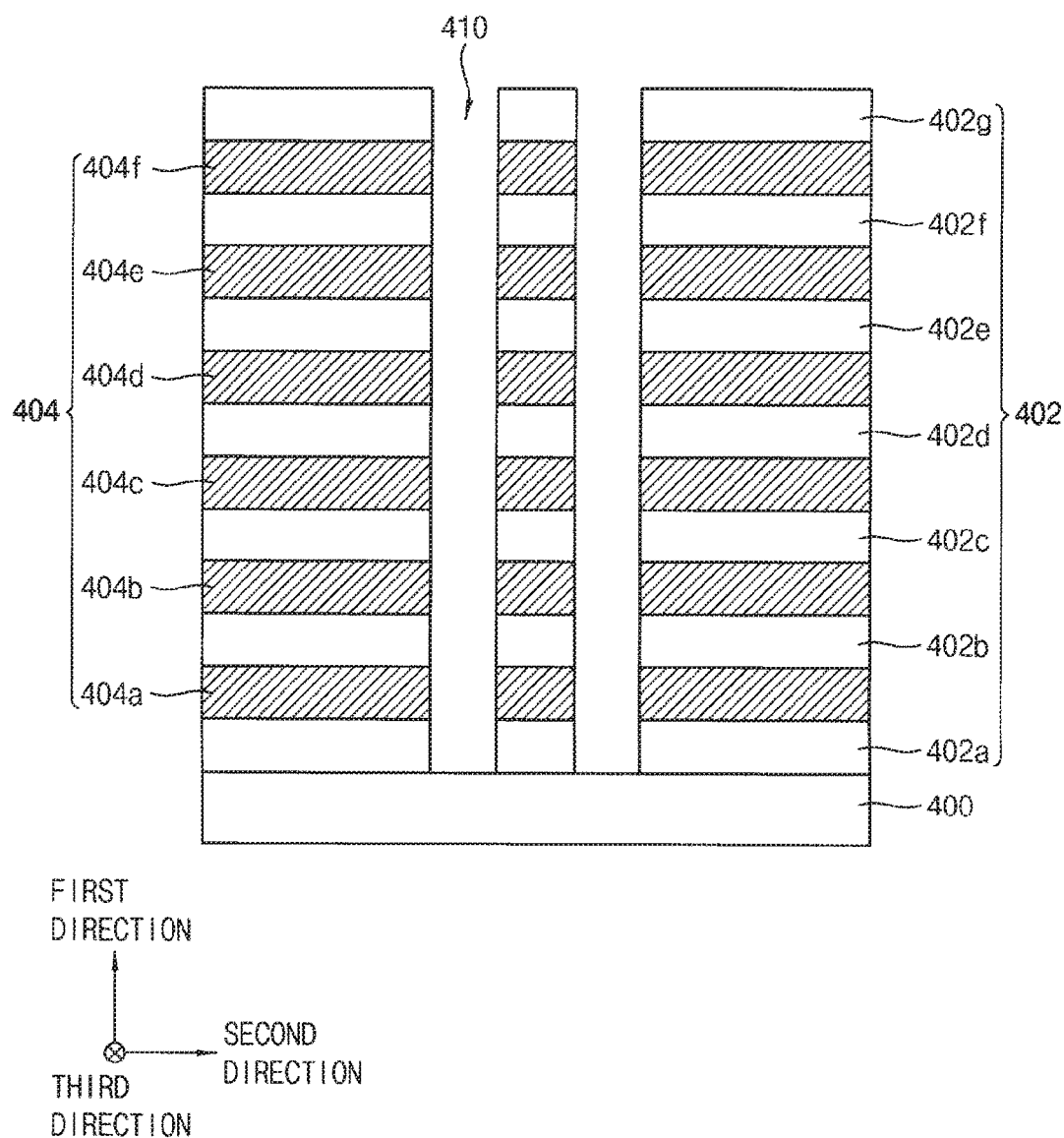

Referring to FIG. 20, interlayer insulation layers 402 (e.g., 402a through 402g) and sacrificial layers 404 (e.g., 404a through 404f) may be alternately and repeatedly formed on a substrate 400 to form a mold structure. Thereafter, the mold structure may be partially etched to form channel holes 410 exposing an upper surface of the substrate 400.

For example, the interlayer insulation layers 402 may include silicon oxide. The sacrificial layers 404 may include a material that may have an etching selectivity with respect to the interlayer insulation layers 402 and may be easily removed through a wet etching process. For example, the sacrificial layer 404 may include silicon nitride.

The sacrificial layers 404 may be removed in a subsequent process to provide spaces for a ground selection line (GSL), a word line and a string selection line (SSL). Thus, the number of the interlayer insulation layers 402 and the sacrificial layers 404 may be determined in consideration of the number of the GSL, the word line and the SSL.

For example, each of the GSL and the SSL may be formed at a single level, and the word line may be formed at 4 levels. In this case, the sacrificial layers 404 and the interlayer insulation layers 402 are formed at 6 levels and 7 levels, respectively. However, the number of the interlayer insulation layers 402 and the sacrificial layers 404 are not specifically limited and the number of the interlayer insulation layers 402 and the sacrificial layers 404 may increase or decrease depending on degree of integration of the semiconductor device.

For example, the mold structure may be partially removed through a dry etching process to form a plurality of channel holes 410. In some example embodiments, the channel holes 410 may form a channel hole row along the third direction. In some example embodiments, the channel holes 410 may form a channel hole row along the second direction.

Figure 21:
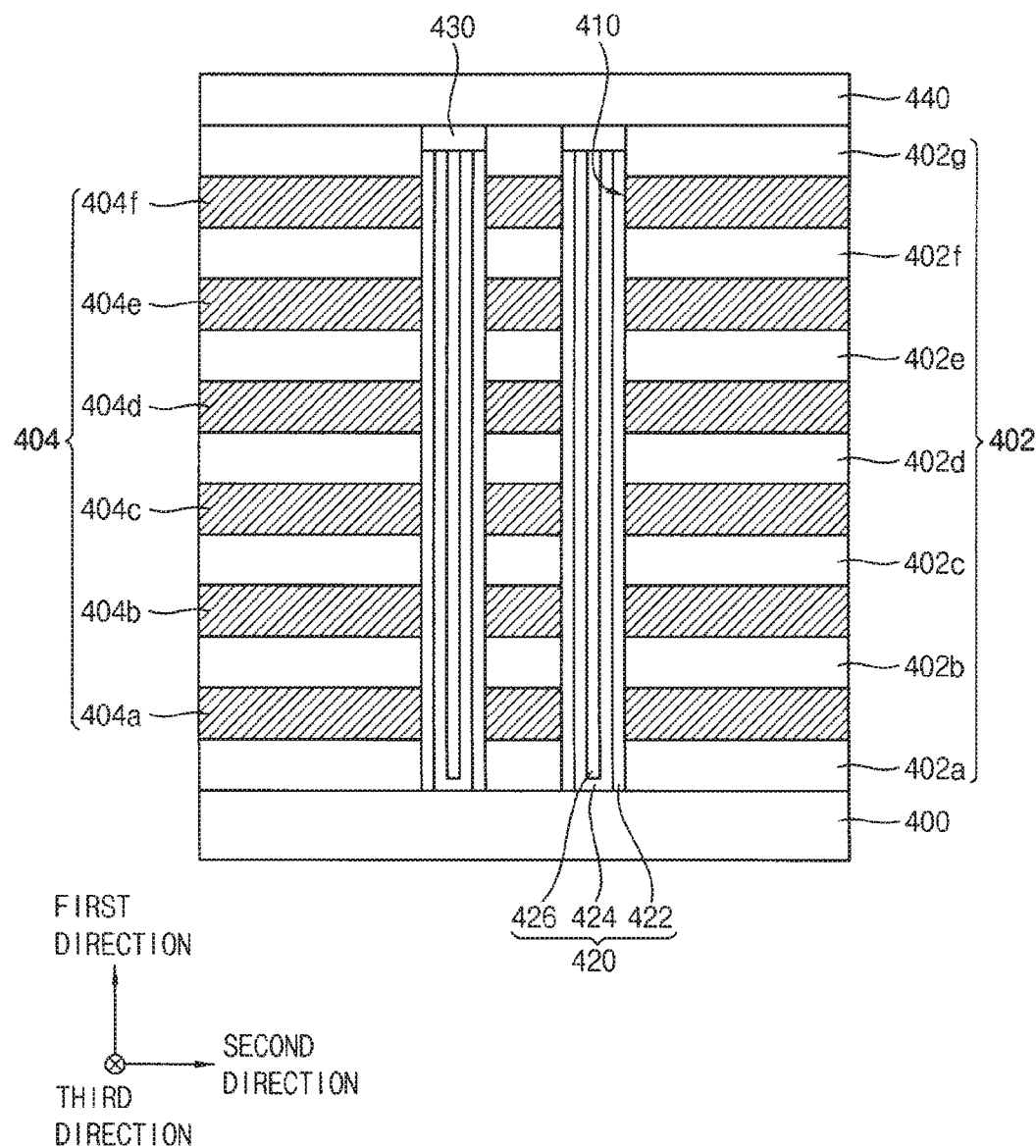

Referring to FIG. 21, a vertical channel structure 420 including a dielectric layer structure 422, a channel 424 and a filling pattern 426 may be formed in each of the channel holes 410. A capping pad 430 may be formed on the vertical channel structure 420.

For example, a dielectric layer may be formed along a sidewall and a bottom surface of the channel holes 410 and an upper surface of the uppermost interlayer insulation layer 402g. For example, a blocking layer, a charge trap layer and a tunnel insulation layer may be sequentially formed to obtain the dielectric layer.

For example, the blocking layer may be formed by using an oxide, such as silicon oxide, the charge trap layer may be formed by using silicon nitride or a metal oxide, and the tunnel insulation layer may be formed by using an oxide such as silicon oxide. For example, the dielectric layer may be formed to have an ONO-layered structure.

For example, upper and lower portions of the dielectric layer may be removed through an etch-back process. Thus, portions of the dielectric layer formed on the upper surfaces of the uppermost interlayer insulation layer 402g and the substrate 400 may be substantially removed to form the dielectric layer structure 422. For example, the dielectric layer structure 422 may be formed at the sidewall of the channel hole 410, and may have a substantially straw shape or a substantially cylindrical shell shape.

Thereafter, a channel layer may be formed on surfaces of the uppermost interlayer insulation layer 402g and the dielectric layer structures 422, and the upper surface of the substrate 400. A filling layer may be formed on the channel layer to fill remaining portions of the channel holes 410.

In some example embodiments, the channel layer may be formed by using polysilicon or amorphous silicon optionally doped with impurities. In some example embodiments, a heat treatment or a laser beam irradiation may be further performed on the channel layer to change polysilicon or amorphous silicon of the channel layer into single crystalline silicon. The filling layer may be formed by using an insulation material such as silicon oxide or silicon nitride.

The filling layer and the channel layer may be planarized, for example, through a CMP process and/or an etch-back process until the uppermost interlayer insulation layer 402g is exposed. Accordingly, a channel 424 and a filling pattern 426 sequentially stacked from an inner wall of the dielectric layer structure 422 may be formed to fill the channel hole 410.

The channel 424 may have a substantially cup shape, and may be in contact with the upper surface of the substrate 400 exposed through the channel hole 410. The filling pattern 426 may have a substantially pillar shape or a solid cylindrical shape.

The channel 424 may be formed in each channel hole 410, and thus a channel row comparable to the channel hole row may be formed.

In some example embodiments, a channel pillar may be further formed to fill a lower portion of the channel hole 410 before forming the dielectric layer structure 422 and the channel 424. The channel pillar may be formed through a selective epitaxial growth (SEG) process using the upper surface of the substrate 400 exposed through the channel hole 410 as a seed. The channel pillar may include polysilicon or single crystalline silicon.

A capping pad 430 capping an upper portion of the channel hole 410 may be further formed on the vertical channel structure 420. For example, upper portions of the dielectric layer structure 422, the channel 424 and the filling pattern 426 may be partially removed through an etch-back process to form a recess. A pad layer may be formed on the uppermost interlayer insulation layer 402g to fill the recess. An upper portion of the pad layer may be planarized, for example, through a CMP process, until the upper surface of the uppermost interlayer insulation layer 402g is exposed, to form the capping pad 430. In some example embodiments, the pad layer may be formed by using polysilicon optionally doped with n-type impurities.

A first upper insulation layer 440 may be formed on the uppermost interlayer insulation layer 402g to cover the capping pads 430. For example, the first upper insulation layer 440 may be formed through a CVD process, a spin coating process or the like, and may include silicon oxide.

Figure 22:
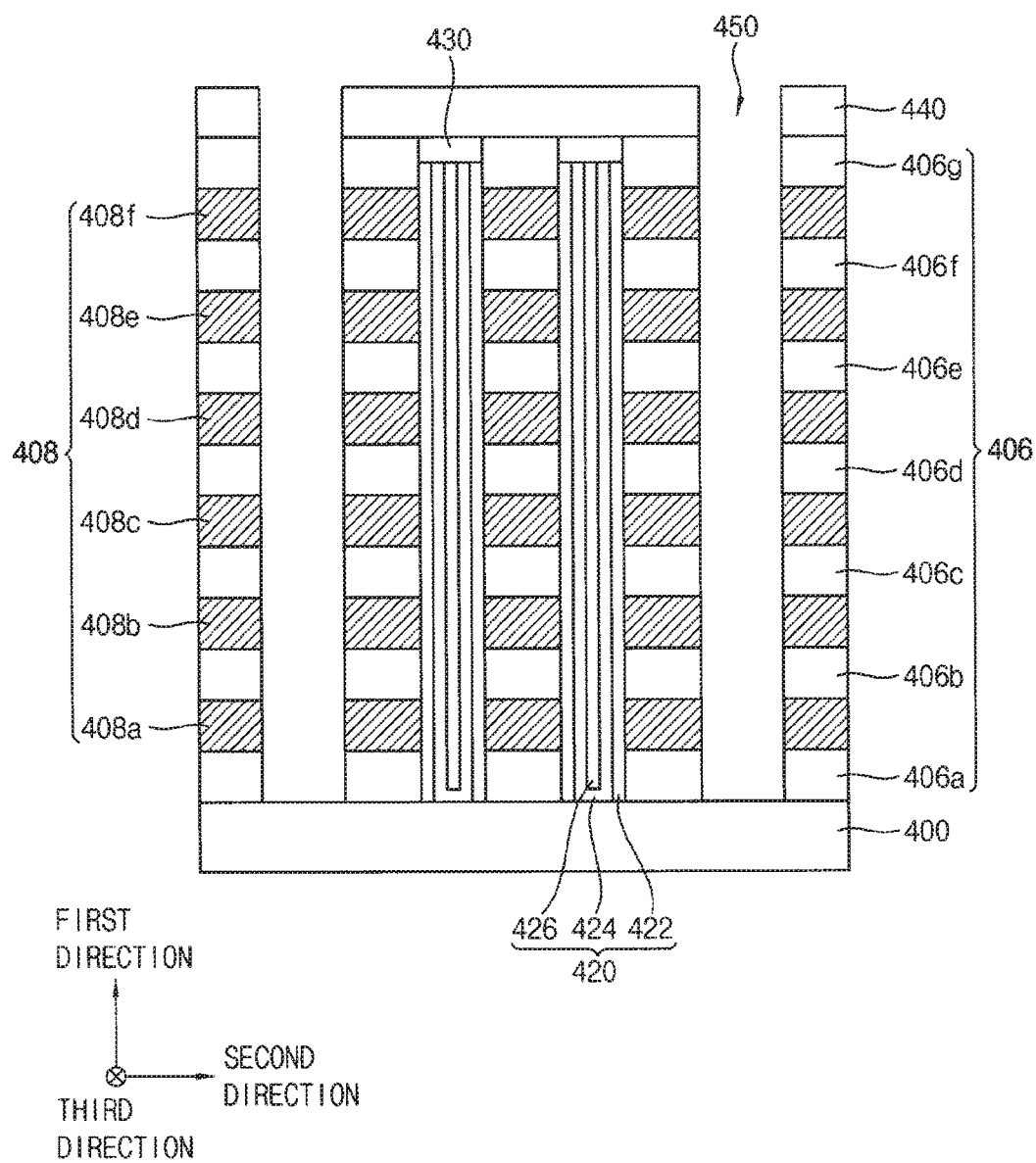

Referring to FIG. 22, the first upper insulation layer 440 and the mold structure may be partially etched to form an opening 450. For example, portions of the first upper insulation layer 440 and the mold structure between channel rows adjacent to each other may be etched through a dry etching process to form the opening 450.

The opening 450 may pass through the mold structure along the first direction to expose the upper surface of the substrate 400. Furthermore, the opening 450 may extend along the third direction, and a plurality of openings 450 may be formed and arranged along the second direction.

The opening 450 may be provided as a gate line cut region. The desired (and/or alternatively predetermined) number of the channel rows may be arranged between the openings 450 adjacent to each other along the second direction.

As the openings 450 are formed, the interlayer insulation layers 402 and the sacrificial layers 404 may be changed into interlayer insulation patterns 406 (e.g., 406a through 406g) and sacrificial patterns 408 (e.g., 408a through 408f). The interlayer insulation layer patterns 406 and the sacrificial patterns 408 at each level may have a plate shape surrounding the vertical channel structures 420 included in the channel rows and extending in a direction.

Figure 23:
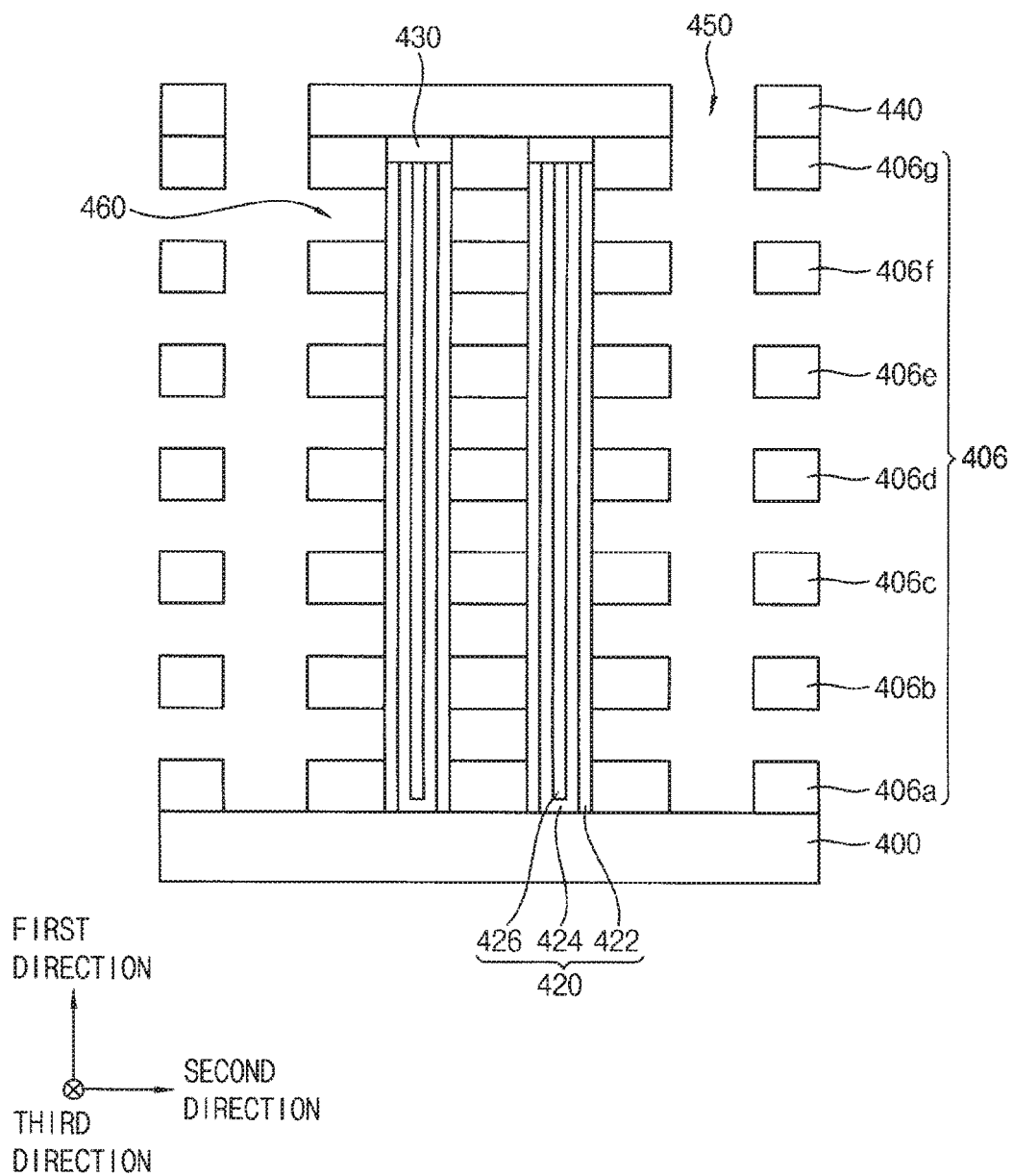

Referring to FIG. 23, the sacrificial patterns 408, of which the sidewalls are exposed by the opening 450, may be removed.

When the sacrificial patterns 408 include silicon nitride, and when the interlayer insulation patterns 406 include silicon oxide, the sacrificial patterns 308 may be removed through a wet etching process using an etchant solution having selectivity with respect to silicon nitride, for example, phosphoric acid.

A gap 460 may be defined by a space from which the sacrificial patterns 408 are removed. A plurality of the gaps 460 may be formed between the adjacent interlayer insulation layer patterns 406. An outer sidewall of the dielectric layer structure 422 may be exposed by the gaps 460.

Figure 24:
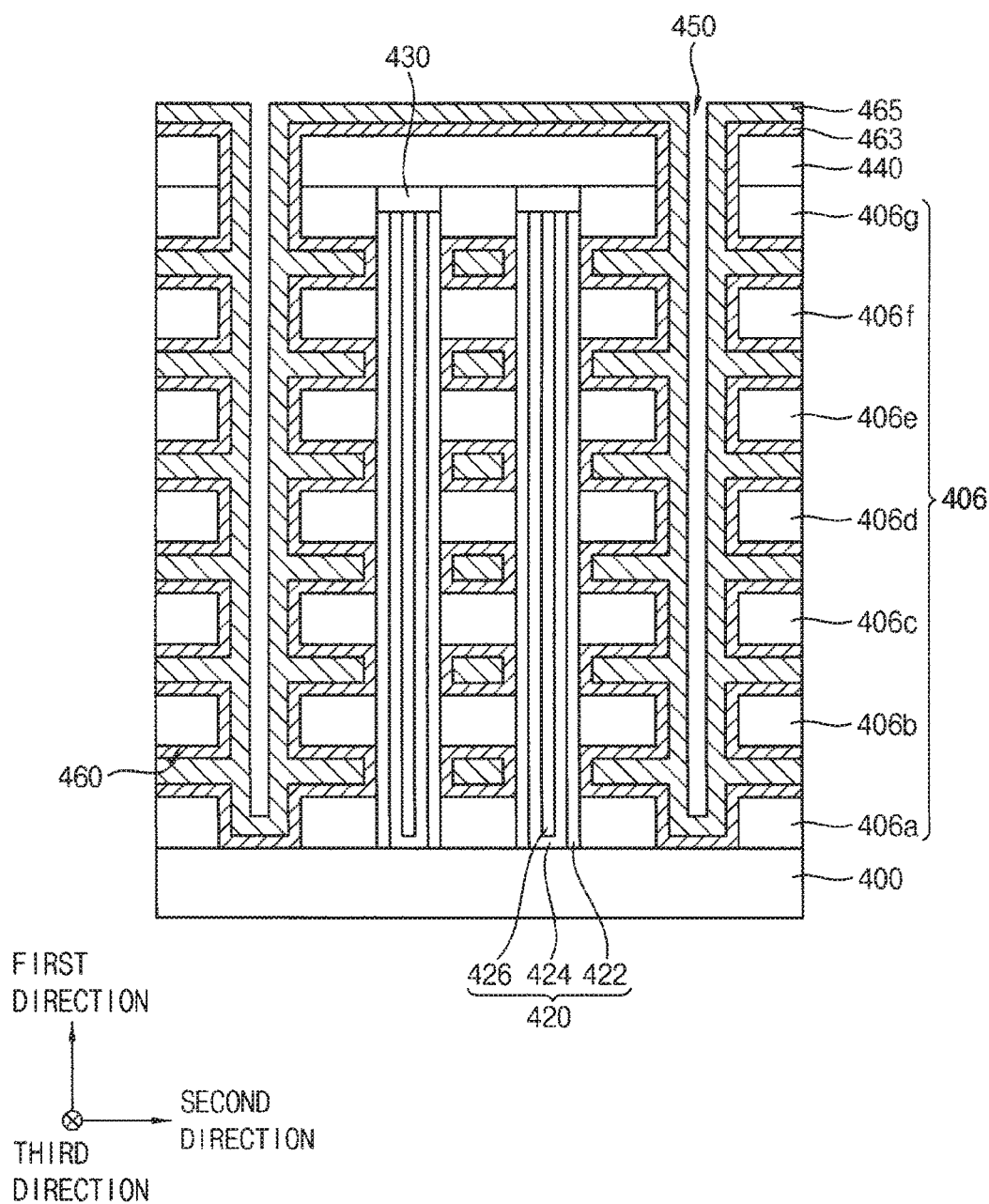

Referring to FIG. 24, a barrier conductive layer 463 may be formed along the exposed outer sidewall of the dielectric layer structure 422, an inner wall of the gap 460, a surface of the interlayer insulation layer pattern 406, and the exposed upper surface of the substrate 400. A metal gate layer 465 may be formed on the barrier conductive layer 463. In some example embodiments, the metal gate layer 465 may sufficiently fill the gap 460, and may at least partially fill the opening 450.

In some example embodiments, the barrier conductive layer 463 may be formed by the method of forming a layer, which is previously explained with reference to FIGS. 1 to 7 or FIGS. 8 to 10, using an organometallic precursor according to some example embodiments.

As previously explained, the organometallic precursor may include tungsten as a central metal, and a cyclopentadienyl ligand bonded to tungsten. The organometallic precursor may further include an allyl ligand. An alkylsilyl ligand may be further bonded to the cyclopentadienyl ligand.

In some example embodiments, the organometallic precursor may include at least one of compounds represented by Chemical Formulas 1 or 2.

The barrier conductive layer 463 including tungsten nitride may be formed through an ALD process or a PEALD process, which is explained with reference to FIGS. 1 to 7 or FIGS. 8 to 10, using the organometallic precursor. The organometallic precursor has increased thermal stability and volatility. Thus, the barrier conductive layer 463 may be formed to have a substantially uniform thickness and increased conformal property on the inner walls of the gaps 460.

In some example embodiments, the metal gate layer 465 may be also formed by using the organometallic precursor according to some example embodiments. For example, providing the organometallic precursor and the purging process may be repeated to form the metal gate layer 465 having a structure having tungsten atomic layers that are vertically deposited. In some example embodiments, the barrier conductive layer 463 and the metal gate layer 465 may be deposited with in-situ in a substantially same vapor deposition chamber.

Figure 25:
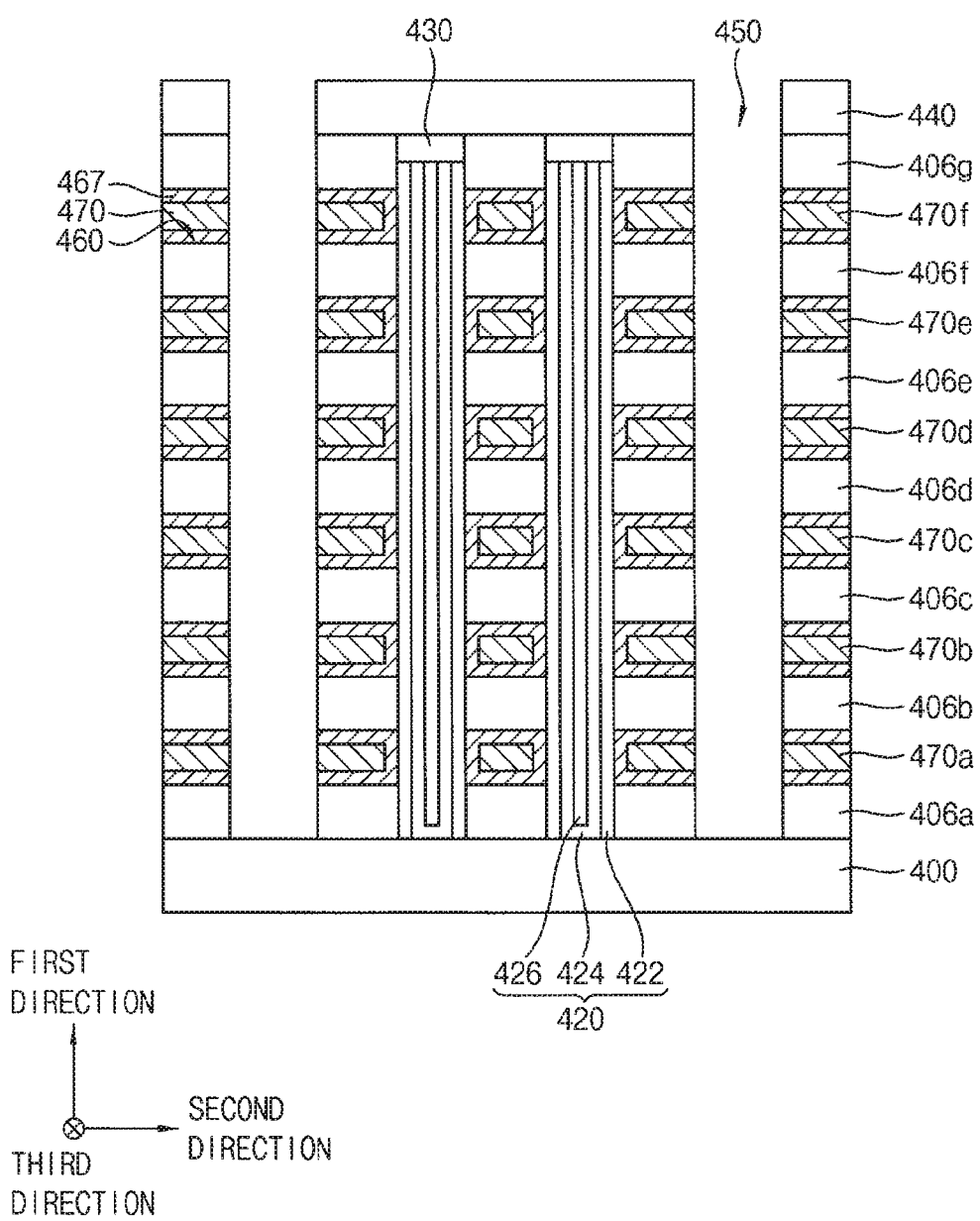

Referring to FIG. 25, the barrier conductive layer 463 and the metal gate layer 465 may be partially etched to form a barrier conducive pattern 467 and a metal gate 470 (e.g., 470a through 470f) in each of the gaps 460. The metal gate 470 may have a linear shape or a plate shape, which surround sidewalls of the vertical channel structures 420 included in the channel rows and extending in direction.

For example, upper portions of the barrier conductive layer 463 and the metal gate layer 465 may be planarized through a CMP process until an upper surface of the first upper insulation layer 440 may be exposed. Thereafter, portions of the barrier conductive layer 463 and the metal gate layer 465 formed in the opening 450 may be etched through an anisotropic etching process to form the barrier conductive pattern 467 and the metal gate 470 in the gap 460 at each levels. The barrier conductive pattern 467 may be formed along the inner wall of the gap 460, and the metal gate 470 may be formed on the barrier conductive pattern 467 to fill the gap 460 at each levels.

The metal gates 470 may include a GSL, a word line and a SSL sequentially stacked from the upper surface of the substrate 400 and spaced apart from one another along the first direction. For example, a lowermost metal gate 470a may be provided as the GSL. The four metal gates 470b to 470e on the GSL may be provided as the word line. An uppermost metal gate 470f on the word line may be provided as the SSL.

Figure 26:
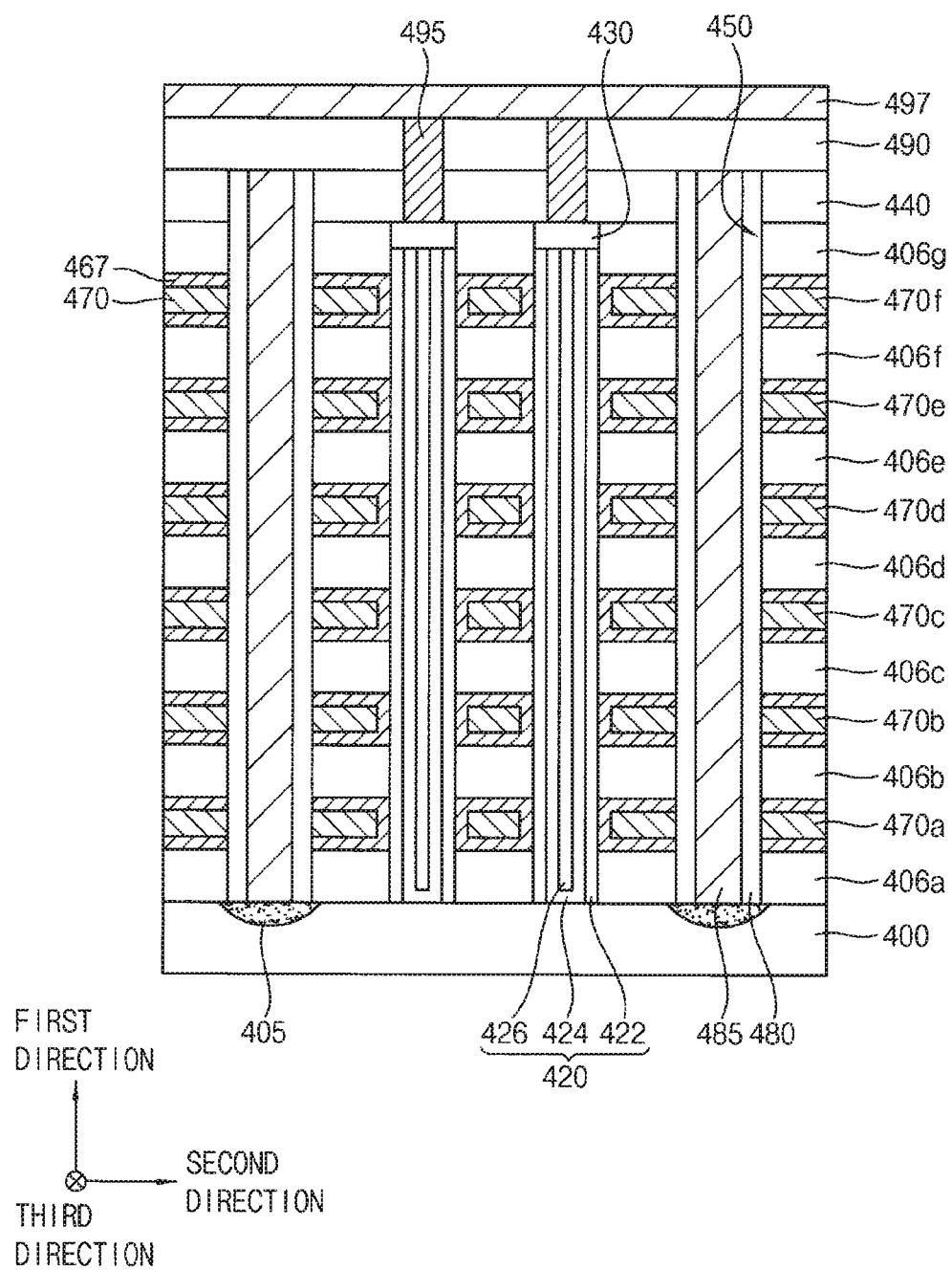

Referring to FIG. 26, an impurity region 405 may be formed on the substrate 400 exposed by the opening 450, and a spacer 480 and a cutting pattern 485 may be formed in the opening 450.

For example, n-typed impurities such as phosphorus or arsenic may be provided through the opening 450, for example, by an ion implantation process to form the impurity region 405. The impurity region 405 may be formed on the substrate 400 and may extend along the third direction.

The spacer 480 may be formed at the sidewall of the opening 450. For example, a spacer layer including an insulation material such as silicon oxide may formed along the upper surface of the first upper insulation layer 440 and the sidewall and the bottom surface of the opening 450 through an ALD process. For example, the spacer layer may be partially removed through an anisotropic etching process or an etch-back process to selectively form the spacer 480 at the sidewall of the opening 450.

Thereafter, the cutting pattern 485 may be formed to fill a remaining portion of the opening 450. For example, a conductive layer may be formed on the first upper insulation layer 440 to sufficiently fill the opening 450. An upper portion of the conductive layer may be planarized through a CMP process, until the upper surface of the first upper insulation layer 440 is exposed, to form the cutting pattern 485 extending in the opening 450.

The conductive layer may include a metal, a metal nitride, a metal silicide and/or polysilicon doped with impurities, and may be formed through an ALD process or a sputtering process. The cutting pattern 485 may be provided as a CSL of the semiconductor device.

In some example embodiments, the conductive layer may be formed by using an organometallic precursor according to some example embodiments. In this case, the cutting pattern 485 may include tungsten.

A second upper insulation layer 490 may be formed on the first upper insulation layer 440 to cover the cutting pattern 485 and the spacer 480. The second upper insulation layer 490 may include silicon oxide substantially similar to or same as the first upper insulation layer 440, and may be formed through a CVD process.

Thereafter, a bit line contact 495 may be formed. The bit line contact 495 may pass through the first and second upper insulation layers 440 and 490 to contact the capping pad 430. Thereafter, a bit line 497 electrically connected to the bit line contact 495 may be formed on the second upper insulation layer 490. The bit line contact 495 and the bit line 497 may include a metal, a metal nitride, polysilicon doped with impurities or the like, and may be formed through a CVD process, an ALD process, a sputtering process or the like.

A plurality of the bit line contacts 495 may be formed to correspond to the capping pad 430 thereby forming a bit line contact array. Furthermore, the bit line 497 may extend along the second direction, and may be electrically connected to a plurality of the capping pads 430 through the bit line contact 495. Furthermore, a plurality of the bit lines 497 may be formed along the third direction.

Hereinafter, an organometallic precursor and a method of forming a layer using an organometallic precursor according to some example embodiments will be more fully explained with reference specific synthetic examples and experimental examples.

Synthetic Example 1: (ethyl cyclopentadienyl)(2-methylallyl)(dicarbonyl)tungsten [(EtCp)(2-Meallyl)W(CO)2]

A 100 g (0.231 mol) of (tripropionitrile)(tricarbonyl)tungsten and 1,000 ml of propionitrile were injected into a flame-dried 3,000 mL flask under an atmosphere of nitrogen gas. Then, 167.2 g (1.847 mol) of 1-chloro-2-methylpropene was added thereto with the solution stirred. The reaction solution was stirred for five hours at 25° C., and then vacuum-treated for concentration. Thereafter, 1,000 ml of diethyl ether was added to form precipitate having a reddish brown color. After the precipitate was vacuum-filtrated, a solvent was removed from obtained solid including (2-methylallyl)(dicarbonyl)(dipropionitrile)tungsten by vacuum. Then, 100 g (0.242 mol) of the solvent-removed solid, (2-methylallyl)(dicarbonyl)(dipropionitrile)tungsten, and 24.26 g (0.242 mol) of lithium ethyl cyclopentadiene were injected into a flame-dried 2,000 mL flask under an atmosphere of nitrogen gas, and 1,000 ml of tetrahydrofuran (THF) was added thereto. After the solution was stirred for eighteen hours at 25° C., the solution was filtrated to remove lithium chloride, which was byproduct. The remaining solution was vacuum-treated to remove a solvent.

In order to increase purity of remaining material, the remaining solution was vacuum-distilled (95° C., 0.4 mmHg) to obtain 69 g of (ethylcyclopentadienyl)(2-methylallyl)(dicarbonyl)tungsten, which is represented by Chemical Formula 2-1 as reddish brown liquid with 73% of yield (1H NMR(C6D6): δ 4.56 (4H, s), 2.79 (2H, s), 2.28 (3H, s), 1.87 (2H, q), 1.41 (2H, s), 0.81 (3H, t)).

Synthetic Example 2: (dimethylpropylsilyl cyclopentadienyl)methyl (tricarbonyl)tungsten [(CpSiMe2Pr)W(Me)(CO)3]

A 88.8 g (0.23 mol) of (tripropionitrile)(tricarbonyl)tungsten and 500 ml of THF were injected into a flame-dried 3,000 mL flask under an atmosphere of nitrogen gas. 39.1 g (0.23 mol) of lithium dimethylpropylsilyl cyclopentadiene dissolved in 500 ml of THF was slowly added thereto at −10° C. with the solution stirred. The reaction solution was stirred for three hours at 25° C., and 32.2 g (0.23 mol) of methyl iodide was slowly added thereto at a room temperature. After stirred for two hours at 25° C., the reaction solution was filtrated to remove solid byproduct, and the remaining solution was vacuum-treated to remove a solvent.

In order to increase purity of remaining material, the remaining solution was vacuum-distillated (120° C., 0.7 mmHg) to obtain 53.9 g of dimethylpropylsilyl cyclopentadienyl)methyl(tricarbonyl)tungsten, which is represented by Chemical Formula 1-4 as orange liquid with 53% of yield (1H NMR(C6D6): δ 4.69 (2H, s), 4.48 (2H, s), 1.17 (2H, m), 0.89 (3H, t), 0.50 (3H, s), 0.47 (2H, m), 0.06 (6H, s)).

Experimental Example 1

A silicon substrate was loaded in a vapor deposition chamber for PEALD, a temperature of the substrate was adjusted to be 400° C. (Ethylcyclopentadienyl)(2-methylallyl)(dicarbonyl)tungsten of Synthetic Example 1 was injected as an organometallic precursor from a stainless steel bubbler container, and the temperature was adjusted to be 115° C. The organometallic precursor was provided into the vapor deposition chamber with argon gas as transferring gas (50 sccm) for 15 seconds. Purging was performed with argon gas (1,100 sccm) for 15 seconds to remove byproduct and the organometallic precursor remaining in the vapor deposition chamber. Ammonia gas was injected as reaction gas (2,000 sccm) for 25 seconds to form a tungsten thin film. Thereafter, purging was performed again with argon gas (960 sccm) for 10 seconds to remove byproduct and the reaction gas remaining in the vapor deposition chamber. The above processes were repeated by 300 cycles to form a tungsten-containing thin film having a thickness of 200 Å. As a result of AES analysis of the tungsten-containing thin film, amounts of tungsten and nitrogen were 30.4% and 14.4%, respectively. Thus, it can be noted that a tungsten nitride layer was substantially formed.

Experimental Example 2

A silicon substrate was loaded in a vapor deposition chamber for PEALD, a temperature of the substrate was adjusted to be 250° C. Dimethylpropylsilyl cyclopentadienyl)methyl(tricarbonyl)tungsten of Synthetic Example 2 was injected as an organometallic precursor from a stainless steel bubbler container, and the temperature was adjusted to be 128° C. The organometallic precursor was provided into the vapor deposition chamber with argon gas as transferring gas (50 sccm) for 5 seconds. Purging was performed with argon gas (3,000 sccm) for 10 seconds to remove byproduct and the organometallic precursor remaining in the vapor deposition chamber. Hydrogen gas was injected as reaction gas (500 sccm with RF power 400 W) for 10 seconds to form a tungsten thin film. Thereafter, purging was performed again with argon gas (3,000 sccm) for 10 seconds to remove byproduct and the reaction gas remaining in the vapor deposition chamber. The above processes were repeated by 500 cycles to form a tungsten-containing thin film having a thickness of 260 Å. As a result of AES analysis of the tungsten-containing thin film, amounts of tungsten and carbon were 20% and 30%, respectively. Thus, it can be noted that a tungsten carbide layer was substantially formed.

Organometallic precursors according to some example embodiments of inventive concepts may be used for forming a conductive structure such as a contact of a DRAM device, a gate pattern of flash memory device or the like. Furthermore, the organometallic precursors may be used for forming an electrode, a gate, a contact or the like for various semiconductor devices such as an MRAM device, an ReRAM device, a PRAM device, a login element or the like.

The foregoing is illustrative of example embodiments and is not to be construed as limiting thereof. Although a few example embodiments have been described, those skilled in the art will readily appreciate that many modifications are possible without materially departing from the novel teachings, features, and effects of inventive concepts. Accordingly, all such modifications are intended to be included within the scope of the claims.

What is claimed is:
1. A method of manufacturing a semiconductor device, the method comprising:
   forming a barrier conductive layer by providing an organometallic precursor on a semiconductor substrate, the organometallic precursor being represented by one of the following Chemical Formulae 1-3 or 1-4,

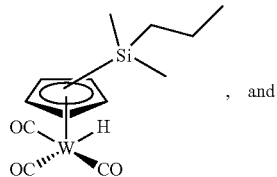
, and [Chemical Formula 1-3]

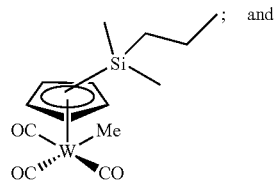
; and [Chemical Formula 1-4]

forming a metal layer on the barrier conductive layer.
2. The method of claim 1, wherein
   the forming the barrier conductive layer includes providing a nitrogen-containing gas over the substrate during the providing the organometallic precursor, and
   the forming the forming the barrier conductive layer includes forming the barrier conductive layer as a tungsten nitride layer.
3. The method of claim 2, wherein
   the forming the metal layer includes providing the organometallic precursor on the barrier conductive layer, and
   the metal layer includes a tungsten layer.
4. The method of claim 3, wherein the forming the metal layer includes providing the organometallic precursor on the barrier conductive layer with a hydrogen gas.
5. A method of forming a layer comprising:
   forming a precursor thin film on a substrate,
      the precursor thin film including an organometallic precursor,
   the organometallic precursor being represented by one of the following Chemical Formulae 1-3 or 1-4,

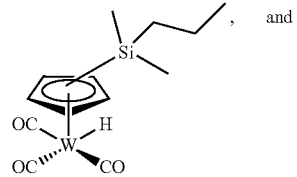
, and [Chemical Formula 1-3]

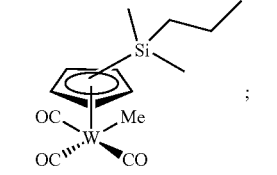
; [Chemical Formula 1-4]

forming a metal nitride layer by providing a reaction gas over the precursor thin film, the reaction gas including a nitrogen-containing gas; and forming a plurality of metal nitride layers by repeating the forming the precursor thin film and the forming the metal nitride layer at least one time.

6. The method of claim 5, further comprising:
forming a plurality of reaction material layers alternately stacked with the plurality of metal nitride layers, wherein
the forming the plurality of reaction material layers includes forming a metal atomic layer on a corresponding one of the plurality of metal nitride layers and providing the reaction gas over the metal atomic layer before forming a next one of the plurality of metal nitride layers.

7. The method of claim 5, wherein
the forming the plurality of metal nitride layers is performed in a process chamber while the process chamber is maintained at a temperature in a range of range of about 200° C. to about 600° C.

* * * * *